US009398956B2

(12) United States Patent
Hazebrouck et al.

(10) Patent No.: US 9,398,956 B2
(45) Date of Patent: *Jul. 26, 2016

(54) FIXED-BEARING KNEE PROSTHESIS HAVING INTERCHANGEABLE COMPONENTS

(71) Applicant: DEPUY (IRELAND), Cork (IE)

(72) Inventors: Stephen A. Hazebrouck, Winona Lake, IN (US); Daren L. Deffenbaugh, Winona Lake, IN (US); Mark A. Heldreth, Mentone, IN (US); Jack T Bryant, Warsaw, IN (US); Rusty T. Meier, Warsaw, IN (US)

(73) Assignee: DEPUY (IRELAND), Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/788,935

(22) Filed: Mar. 7, 2013

(65) Prior Publication Data
US 2013/0184830 A1 Jul. 18, 2013

Related U.S. Application Data

(63) Continuation of application No. 12/904,614, filed on Oct. 14, 2010, now Pat. No. 8,632,600, which is a continuation-in-part of application No. 12/620,034, filed on Nov. 17, 2009, now Pat. No. 8,128,703, which is a continuation-in-part of application No. 11/863,318, filed on Sep. 28, 2007, now Pat. No. 7,628,818.

(51) Int. Cl.
*A61F 2/38* (2006.01)
*A61F 2/42* (2006.01)
*A61F 2/30* (2006.01)

(52) U.S. Cl.
CPC . *A61F 2/38* (2013.01); *A61F 2/389* (2013.01); *A61F 2/3859* (2013.01); *A61F 2/4202* (2013.01);

(Continued)

(58) Field of Classification Search
CPC .................. A61F 2/3868; A61F 2/389; A61F 2002/30172
USPC .......... 623/20.14, 20.15, 20.27–20.29, 20.31, 623/20.33
See application file for complete search history.

(56) References Cited

U.S. PATENT DOCUMENTS 3,453,104 A 7/1969 de Marchi et al.
3,645,793 A 2/1972 Hein et al.

(Continued)

FOREIGN PATENT DOCUMENTS

CN 1429185 A 7/2003
CN 101007345 A 8/2007

(Continued)

OTHER PUBLICATIONS

Carl Zeiss, Zeiss Surfcomm 5000—"Contour and Surface Measuring Machines," 2005, 16 pages.

(Continued)

*Primary Examiner* — Alvin Stewart
(74) *Attorney, Agent, or Firm* — Barnes & Thornburg LLP

(57) ABSTRACT

A fixed-bearing prosthesis includes a femoral component having a medial condyle surface and a lateral condyle surface. The knee prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. A posterior buttress extends along a posterior section of the perimeter of the tray's platform, and an anterior buttress extends along an anterior section of the perimeter of the tray's platform. Differently-sized tibial trays are interchangeable with differently-sized bearings.

19 Claims, 8 Drawing Sheets

(52) U.S. Cl.
CPC . *A61F 2002/305* (2013.01); *A61F 2002/30013* (2013.01); *A61F 2002/3092* (2013.01); *A61F 2002/30143* (2013.01); *A61F 2002/30332* (2013.01); *A61F 2002/30604* (2013.01); *A61F 2002/30878* (2013.01); *A61F 2002/30957* (2013.01); *A61F 2002/30968* (2013.01); *A61F 2220/0025* (2013.01); *A61F 2220/0033* (2013.01); *A61F 2230/0017* (2013.01); *A61F 2250/0024* (2013.01); *A61F 2310/00796* (2013.01)

(56) References Cited

U.S. PATENT DOCUMENTS

| | | | |
|---|---|---|---|
| 3,852,045 A | 12/1974 | Wheeler et al. | |
| 3,855,638 A | 12/1974 | Pilliar | |
| 3,953,899 A | 5/1976 | Charnley | |
| D248,771 S | 8/1978 | Groth, Jr. et al. | |
| 4,145,764 A | 3/1979 | Suzuki et al. | |
| 4,156,943 A | 6/1979 | Collier | |
| 4,206,516 A | 6/1980 | Pilliar | |
| 4,224,696 A | 9/1980 | Murray et al. | |
| 4,224,697 A | 9/1980 | Murray et al. | |
| 4,257,129 A * | 3/1981 | Volz | 623/20.33 |
| 4,479,271 A | 10/1984 | Bolesky et al. | |
| 4,508,841 A | 4/1985 | Onuma et al. | |
| 4,550,448 A | 11/1985 | Kenna | |
| 4,612,160 A | 9/1986 | Donlevy et al. | |
| 4,673,407 A | 6/1987 | Martin | |
| 4,693,721 A | 9/1987 | Ducheyne | |
| 4,714,474 A | 12/1987 | Brooks, Jr. et al. | |
| 4,725,588 A | 2/1988 | Snyder et al. | |
| 4,778,474 A | 10/1988 | Homsy | |
| 4,795,468 A | 1/1989 | Hodorek et al. | |
| 4,808,185 A | 2/1989 | Penenberg et al. | |
| 4,822,362 A | 4/1989 | Walker et al. | |
| 4,838,891 A | 6/1989 | Branemark et al. | |
| 4,923,473 A | 5/1990 | Griss et al. | |
| 4,938,769 A * | 7/1990 | Shaw | 623/20.15 |
| 4,944,757 A * | 7/1990 | Martinez et al. | 623/20.15 |
| 4,944,760 A | 7/1990 | Kenna | |
| 4,950,298 A | 8/1990 | Gustilo et al. | |
| 4,954,170 A | 9/1990 | Fey et al. | |
| 4,955,919 A | 9/1990 | Pappas et al. | |
| 4,963,152 A | 10/1990 | Hofmann et al. | |
| 4,969,904 A | 11/1990 | Koch et al. | |
| 4,969,907 A | 11/1990 | Koch et al. | |
| 4,990,163 A | 2/1991 | Ducheyne et al. | |
| 5,019,103 A | 5/1991 | Van Zile et al. | |
| 5,030,233 A | 7/1991 | Ducheyne | |
| 5,037,423 A | 8/1991 | Kenna | |
| 5,080,674 A | 1/1992 | Jacobs et al. | |
| 5,080,675 A | 1/1992 | Lawes et al. | |
| 5,104,410 A | 4/1992 | Chowdhary | |
| 5,108,442 A | 4/1992 | Smith | |
| 5,152,797 A | 10/1992 | Luckman et al. | |
| 5,171,283 A | 12/1992 | Pappas et al. | |
| 5,176,710 A | 1/1993 | Hahn et al. | |
| 5,194,066 A | 3/1993 | Van Zile | |
| 5,198,308 A | 3/1993 | Shetty et al. | |
| 5,201,766 A | 4/1993 | Georgette | |
| 5,201,768 A | 4/1993 | Caspari et al. | |
| 5,226,917 A | 7/1993 | Schryver | |
| 5,251,468 A | 10/1993 | Lin et al. | |
| 5,258,044 A | 11/1993 | Lee | |
| 5,263,987 A | 11/1993 | Shah | |
| 5,271,737 A | 12/1993 | Baldwin et al. | |
| 5,282,861 A | 2/1994 | Kaplan | |
| 5,308,556 A | 5/1994 | Bagley | |
| 5,309,639 A | 5/1994 | Lee | |
| 5,310,408 A | 5/1994 | Schryver et al. | |
| 5,326,361 A | 7/1994 | Hollister | |
| 5,326,365 A | 7/1994 | Alvine et al. | |
| 5,330,534 A * | 7/1994 | Herrington et al. | 623/20.27 |
| 5,344,460 A | 9/1994 | Turanyi et al. | |
| 5,344,461 A | 9/1994 | Phlipot | |
| 5,344,494 A | 9/1994 | Davison et al. | |
| 5,358,531 A * | 10/1994 | Goodfellow et al. | 623/20.29 |
| 5,360,452 A | 11/1994 | Engelhardt et al. | |
| 5,368,881 A | 11/1994 | Kelman et al. | |
| 5,370,699 A | 12/1994 | Hood et al. | |
| 5,387,240 A * | 2/1995 | Pottenger et al. | 623/20.29 |
| 5,405,396 A | 4/1995 | Heldreth et al. | |
| 5,409,650 A | 4/1995 | Holme | |
| 5,413,604 A | 5/1995 | Hodge | |
| 5,414,049 A | 5/1995 | Sun et al. | |
| 5,443,510 A | 8/1995 | Shetty et al. | |
| 5,449,745 A | 9/1995 | Sun et al. | |
| 5,454,365 A | 10/1995 | Bonutti | |
| 5,458,637 A | 10/1995 | Hayes | |
| 5,480,444 A | 1/1996 | Incavo | |
| 5,480,445 A | 1/1996 | Burkinshaw | |
| 5,480,446 A | 1/1996 | Goodfellow et al. | |
| 5,507,815 A | 4/1996 | Wagner et al. | |
| 5,534,032 A | 7/1996 | Hodorek | |
| 5,543,471 A | 8/1996 | Sun et al. | |
| 5,549,691 A | 8/1996 | Harwin | |
| 5,549,699 A | 8/1996 | MacMahon et al. | |
| 5,549,701 A | 8/1996 | Mikhail | |
| 5,571,187 A | 11/1996 | Devanathan | |
| 5,571,198 A | 11/1996 | Drucker et al. | |
| 5,605,491 A | 2/1997 | Yam et al. | |
| 5,609,639 A | 3/1997 | Walker | |
| 5,609,641 A | 3/1997 | Johnson et al. | |
| 5,609,648 A | 3/1997 | Oehy et al. | |
| 5,632,745 A | 5/1997 | Schwartz | |
| 5,645,594 A | 7/1997 | Devanathan et al. | |
| 5,645,606 A | 7/1997 | Oehy et al. | |
| 5,650,485 A | 7/1997 | Sun et al. | |
| 5,658,333 A | 8/1997 | Kelman et al. | |
| 5,658,341 A | 8/1997 | Delfosse | |
| 5,658,342 A | 8/1997 | Draganich et al. | |
| 5,658,344 A * | 8/1997 | Hurlburt | 623/20.19 |
| 5,683,472 A | 11/1997 | O'Neil et al. | |
| 5,690,636 A | 11/1997 | Wildgoose et al. | |
| 5,702,447 A | 12/1997 | Walch et al. | |
| 5,702,458 A | 12/1997 | Burstein et al. | |
| 5,702,463 A | 12/1997 | Pothier et al. | |
| 5,702,464 A * | 12/1997 | Lackey et al. | 623/20.32 |
| 5,702,475 A | 12/1997 | Zahedi et al. | |
| 5,725,580 A | 3/1998 | Cloutier et al. | |
| 5,725,588 A | 3/1998 | Errico et al. | |
| 5,728,748 A | 3/1998 | Sun et al. | |
| 5,732,469 A | 3/1998 | Hamamoto et al. | |
| 5,749,874 A | 5/1998 | Schwartz | |
| 5,755,800 A | 5/1998 | O'Neil et al. | |
| 5,755,801 A * | 5/1998 | Walker et al. | 623/20.21 |
| 5,755,803 A | 5/1998 | Haines et al. | |
| 5,755,808 A | 5/1998 | DeCarlo et al. | |
| 5,759,190 A | 6/1998 | Vibe-Hansen et al. | |
| 5,765,095 A | 6/1998 | Flak et al. | |
| 5,766,257 A | 6/1998 | Goodman et al. | |
| 5,769,899 A | 6/1998 | Schwartz et al. | |
| 5,800,546 A | 9/1998 | Marik et al. | |
| 5,800,557 A * | 9/1998 | Elhami | 623/23.12 |
| 5,824,100 A | 10/1998 | Kester et al. | |
| 5,824,103 A | 10/1998 | Williams | |
| 5,847,012 A | 12/1998 | Shalaby et al. | |
| 5,855,601 A | 1/1999 | Bessler et al. | |
| 5,868,797 A | 2/1999 | Pappas et al. | |
| 5,871,545 A * | 2/1999 | Goodfellow et al. | 623/20.28 |
| 5,871,546 A * | 2/1999 | Colleran et al. | 623/20.28 |
| 5,876,456 A | 3/1999 | Sederholm et al. | |
| 5,879,387 A | 3/1999 | Jones et al. | |
| 5,879,389 A | 3/1999 | Koshino et al. | |
| 5,879,394 A * | 3/1999 | Ashby et al. | 623/20.33 |
| 5,879,398 A | 3/1999 | Swarts et al. | |
| 5,879,400 A | 3/1999 | Merrill et al. | |
| 5,888,205 A | 3/1999 | Pratt et al. | |
| 5,902,315 A | 5/1999 | DuBois | |
| 5,906,577 A | 5/1999 | Beane et al. | |
| 5,906,596 A | 5/1999 | Tallarida | |
| 5,906,644 A | 5/1999 | Powell | |

(56) References Cited

U.S. PATENT DOCUMENTS

| | | | |
|---|---|---|---|
| 5,911,758 A | 6/1999 | Oehy et al. | |
| 5,925,077 A | 7/1999 | Williamson et al. | |
| 5,938,698 A | 8/1999 | Sandoz et al. | |
| 5,951,564 A | 9/1999 | Schroder et al. | |
| 5,951,603 A | 9/1999 | O'Neil et al. | |
| 5,957,949 A | 9/1999 | Leonhardt et al. | |
| 5,957,979 A | 9/1999 | Beckman et al. | |
| 5,964,808 A * | 10/1999 | Blaha et al. | 623/20.28 |
| 5,976,147 A | 11/1999 | LaSalle et al. | |
| 5,984,969 A | 11/1999 | Matthews et al. | |
| 5,989,027 A | 11/1999 | Wagner et al. | |
| 5,997,577 A | 12/1999 | Herrington et al. | |
| 6,004,351 A | 12/1999 | Tomita et al. | |
| 6,005,018 A | 12/1999 | Cicierega et al. | |
| 6,010,534 A | 1/2000 | O'Neil et al. | |
| 6,017,975 A | 1/2000 | Saum et al. | |
| 6,039,764 A * | 3/2000 | Pottenger et al. | 623/20.32 |
| 6,042,780 A | 3/2000 | Huang | |
| 6,053,945 A | 4/2000 | O'Neil et al. | |
| 6,059,949 A | 5/2000 | Gal-Or et al. | |
| 6,068,658 A * | 5/2000 | Insall et al. | 623/20.3 |
| 6,087,553 A | 7/2000 | Cohen et al. | |
| 6,090,144 A | 7/2000 | Letot et al. | |
| 6,096,084 A * | 8/2000 | Townley | 623/23.12 |
| 6,117,175 A | 9/2000 | Bosredon | |
| 6,120,541 A | 9/2000 | Johnson | |
| 6,120,546 A | 9/2000 | Dye et al. | |
| 6,123,728 A * | 9/2000 | Brosnahan et al. | 623/20.24 |
| 6,123,896 A | 9/2000 | Meeks, III et al. | |
| 6,126,692 A | 10/2000 | Robie et al. | |
| 6,132,468 A | 10/2000 | Mansmann | |
| 6,135,857 A | 10/2000 | Shaw et al. | |
| 6,139,581 A | 10/2000 | Engh et al. | |
| 6,142,936 A | 11/2000 | Beane et al. | |
| 6,152,962 A | 11/2000 | DeCarlo et al. | |
| 6,162,254 A * | 12/2000 | Timoteo | 623/20.33 |
| 6,165,223 A | 12/2000 | Metzger et al. | |
| 6,168,614 B1 | 1/2001 | Andersen et al. | |
| 6,171,340 B1 | 1/2001 | McDowell | |
| 6,174,934 B1 | 1/2001 | Sun et al. | |
| 6,179,876 B1 | 1/2001 | Stamper et al. | |
| 6,183,519 B1 | 2/2001 | Bonnin et al. | |
| 6,206,881 B1 | 3/2001 | Frigg et al. | |
| 6,210,444 B1 | 4/2001 | Webster et al. | |
| 6,210,445 B1 | 4/2001 | Zawadzki | |
| 6,217,618 B1 | 4/2001 | Hileman | |
| 6,228,900 B1 | 5/2001 | Shen et al. | |
| 6,238,434 B1 | 5/2001 | Pappas | |
| 6,242,507 B1 | 6/2001 | Saum et al. | |
| 6,245,276 B1 | 6/2001 | McNulty et al. | |
| 6,251,143 B1 | 6/2001 | Schwartz et al. | |
| 6,258,127 B1 | 7/2001 | Schmotzer | |
| 6,280,476 B1 | 8/2001 | Metzger et al. | |
| 6,281,264 B1 | 8/2001 | Salovey et al. | |
| 6,293,971 B1 | 9/2001 | Nelson et al. | |
| 6,299,646 B1 * | 10/2001 | Chambat et al. | 623/20.33 |
| 6,312,473 B1 | 11/2001 | Oshida | |
| 6,316,158 B1 | 11/2001 | Saum et al. | |
| 6,319,283 B1 | 11/2001 | Insall et al. | |
| 6,319,285 B1 | 11/2001 | Chamier et al. | |
| 6,344,059 B1 | 2/2002 | Krakovits et al. | |
| 6,352,558 B1 | 3/2002 | Spector | |
| 6,361,564 B1 * | 3/2002 | Marceaux et al. | 623/20.29 |
| 6,372,814 B1 | 4/2002 | Sun et al. | |
| 6,379,388 B1 * | 4/2002 | Ensign et al. | 623/20.34 |
| 6,425,916 B1 | 7/2002 | Garrison et al. | |
| 6,428,577 B1 * | 8/2002 | Evans et al. | 623/20.29 |
| 6,440,063 B1 | 8/2002 | Beane et al. | |
| 6,443,991 B1 | 9/2002 | Running | |
| 6,468,314 B2 | 10/2002 | Schwartz et al. | |
| 6,485,519 B2 | 11/2002 | Meyers et al. | |
| 6,494,914 B2 | 12/2002 | Brown et al. | |
| 6,503,280 B2 | 1/2003 | Repicci | |
| 6,506,215 B1 | 1/2003 | Letot et al. | |
| 6,506,216 B1 | 1/2003 | McCue et al. | |
| 6,520,964 B2 | 2/2003 | Tallarida et al. | |
| 6,524,522 B2 | 2/2003 | Vaidyanathan et al. | |
| 6,527,754 B1 | 3/2003 | Tallarida et al. | |
| 6,569,202 B2 | 5/2003 | Whiteside | |
| 6,582,470 B1 | 6/2003 | Lee et al. | |
| 6,589,283 B1 | 7/2003 | Metzger et al. | |
| 6,592,787 B2 | 7/2003 | Pickrell et al. | |
| 6,620,198 B2 | 9/2003 | Burnstein et al. | |
| 6,623,526 B1 | 9/2003 | Lloyd | |
| 6,626,950 B2 | 9/2003 | Brown et al. | |
| 6,645,251 B2 * | 11/2003 | Salehi et al. | 623/20.28 |
| 6,652,592 B1 | 11/2003 | Grooms et al. | |
| 6,656,226 B2 | 12/2003 | Yoon | |
| 6,660,039 B1 * | 12/2003 | Evans et al. | 623/20.29 |
| 6,660,224 B2 | 12/2003 | Lefebvre et al. | |
| 6,664,308 B2 | 12/2003 | Sun et al. | |
| 6,679,917 B2 | 1/2004 | Ek | |
| 6,699,291 B1 * | 3/2004 | Augoyard et al. | 623/20.27 |
| 6,702,821 B2 | 3/2004 | Bonutti | |
| 6,716,249 B2 | 4/2004 | Hyde | |
| 6,719,800 B2 | 4/2004 | Meyers et al. | |
| 6,726,724 B2 | 4/2004 | Repicci | |
| 6,740,186 B2 | 5/2004 | Hawkins et al. | |
| 6,755,864 B1 | 6/2004 | Brack et al. | |
| 6,769,434 B2 | 8/2004 | Liddicoat et al. | |
| 6,773,461 B2 | 8/2004 | Meyers et al. | |
| 6,783,548 B2 | 8/2004 | Hyde, Jr. | |
| 6,797,006 B2 | 9/2004 | Hodorek | |
| 6,818,020 B2 | 11/2004 | Sun et al. | |
| 6,846,327 B2 | 1/2005 | Khandkar et al. | |
| 6,849,230 B1 | 2/2005 | Feichtinger | |
| 6,852,272 B2 | 2/2005 | Artz et al. | |
| 6,869,448 B2 * | 3/2005 | Tuke et al. | 623/20.32 |
| 6,875,235 B2 | 4/2005 | Ferree | |
| 6,896,702 B2 | 5/2005 | Collazo | |
| 6,923,832 B1 | 8/2005 | Sharkey et al. | |
| 6,939,380 B2 | 9/2005 | Guzman | |
| 6,942,670 B2 | 9/2005 | Heldreth et al. | |
| 6,945,448 B2 | 9/2005 | Medlin et al. | |
| 6,953,479 B2 | 10/2005 | Carson et al. | |
| 6,972,039 B2 * | 12/2005 | Metzger et al. | 623/20.29 |
| 6,984,248 B2 | 1/2006 | Hyde, Jr. | |
| 6,986,791 B1 * | 1/2006 | Metzger | 623/20.24 |
| 6,994,730 B2 | 2/2006 | Posner | |
| 7,011,687 B2 | 3/2006 | Deffenbaugh et al. | |
| 7,018,418 B2 | 3/2006 | Amrich et al. | |
| 7,018,420 B2 | 3/2006 | Grundei | |
| 7,018,583 B2 | 3/2006 | Berger et al. | |
| 7,025,788 B2 | 4/2006 | Metzger et al. | |
| 7,025,790 B2 | 4/2006 | Parks et al. | |
| 7,048,741 B2 | 5/2006 | Swanson | |
| 7,070,622 B1 * | 7/2006 | Brown et al. | 623/20.14 |
| 7,077,867 B1 | 7/2006 | Pope et al. | |
| 7,087,082 B2 | 8/2006 | Paul et al. | |
| 7,094,259 B2 | 8/2006 | Tarabichi | |
| 7,101,401 B2 | 9/2006 | Brack | |
| 7,108,720 B2 | 9/2006 | Hanes | |
| 7,147,819 B2 | 12/2006 | Bram et al. | |
| 7,175,665 B2 | 2/2007 | German et al. | |
| 7,179,295 B2 | 2/2007 | Kovacevic | |
| 7,189,262 B2 | 3/2007 | Hayes, Jr. et al. | |
| 7,208,013 B1 | 4/2007 | Bonutti | |
| 7,208,222 B2 | 4/2007 | Rolfe et al. | |
| 7,255,715 B2 * | 8/2007 | Metzger | 623/20.17 |
| 7,278,997 B1 | 10/2007 | Mueller et al. | |
| 7,294,149 B2 | 11/2007 | Hozack et al. | |
| 7,297,164 B2 | 11/2007 | Johnson et al. | |
| 7,338,529 B1 | 3/2008 | Higgins | |
| 7,341,602 B2 | 3/2008 | Fell et al. | |
| 7,344,460 B2 | 3/2008 | Gait | |
| 7,357,817 B2 * | 4/2008 | D'Alessio, II | 623/20.15 |
| 7,445,639 B2 | 11/2008 | Metzger et al. | |
| 7,462,199 B2 | 12/2008 | Justin et al. | |
| 7,494,507 B2 | 2/2009 | Dixon et al. | |
| 7,497,874 B1 | 3/2009 | Metzger et al. | |
| 7,524,325 B2 | 4/2009 | Khalili | |
| 7,527,631 B2 * | 5/2009 | Maroney et al. | 606/102 |
| 7,527,650 B2 | 5/2009 | Johnson et al. | |
| 7,534,270 B2 | 5/2009 | Ball | |

(56) References Cited

U.S. PATENT DOCUMENTS

| | | | |
|---|---|---|---|
| 7,544,206 B2 | 6/2009 | Cohn | |
| 7,563,286 B2 | 7/2009 | Gerber et al. | |
| 7,572,295 B2 | 8/2009 | Steinberg | |
| 7,578,850 B2 | 8/2009 | Kuczynski et al. | |
| 7,608,079 B1 | 10/2009 | Blackwell et al. | |
| 7,611,519 B2 | 11/2009 | Lefevre et al. | |
| 7,618,462 B2 | 11/2009 | Ek | |
| 7,628,817 B1 | 12/2009 | Axelson, Jr. et al. | |
| 7,628,818 B2* | 12/2009 | Hazebrouck et al. | 623/20.14 |
| 7,635,390 B1 | 12/2009 | Bonutti | |
| 7,670,381 B2* | 3/2010 | Schwartz | 623/17.17 |
| 7,678,151 B2 | 3/2010 | Ek | |
| 7,678,152 B2 | 3/2010 | Suguro et al. | |
| 7,695,519 B2* | 4/2010 | Collazo | 623/20.15 |
| 7,740,662 B2* | 6/2010 | Barnett et al. | 623/20.33 |
| 7,748,984 B2 | 7/2010 | McAllister et al. | |
| 7,749,229 B1 | 7/2010 | Bonutti | |
| 7,753,960 B2* | 7/2010 | Cipolletti et al. | 623/20.29 |
| 7,758,653 B2 | 7/2010 | Steinberg | |
| 7,766,911 B1 | 8/2010 | Navarro et al. | |
| 7,771,484 B2* | 8/2010 | Campbell | 623/20.34 |
| 7,776,044 B2 | 8/2010 | Pendleton et al. | |
| 7,780,666 B1 | 8/2010 | Navarro et al. | |
| 7,780,674 B2* | 8/2010 | Medley et al. | 606/92 |
| 7,785,327 B1 | 8/2010 | Navarro et al. | |
| 7,790,779 B2 | 9/2010 | Muratoglu | |
| 7,799,038 B2 | 9/2010 | Sogard et al. | |
| 7,799,087 B2* | 9/2010 | Howald et al. | 623/23.12 |
| 7,803,193 B2 | 9/2010 | Steinberg | |
| 7,833,245 B2 | 11/2010 | Kaes et al. | |
| 7,951,204 B2* | 5/2011 | Chambat et al. | 623/20.33 |
| 7,981,159 B2 | 7/2011 | Williams et al. | |
| 7,988,736 B2 | 8/2011 | May et al. | |
| 8,066,770 B2 | 11/2011 | Rivard et al. | |
| 8,070,801 B2 | 12/2011 | Cohn | |
| 8,070,821 B2 | 12/2011 | Roger | |
| 8,100,981 B2 | 1/2012 | Clark et al. | |
| 8,105,367 B2 | 1/2012 | Austin et al. | |
| 8,105,387 B2 | 1/2012 | Barnett et al. | |
| 8,128,703 B2* | 3/2012 | Hazebrouck et al. | 623/20.14 |
| 8,163,027 B2 | 4/2012 | Rhodes et al. | |
| 8,187,335 B2 | 5/2012 | Wyss et al. | |
| 8,192,498 B2 | 6/2012 | Wagner et al. | |
| 8,206,451 B2 | 6/2012 | Wyss et al. | |
| 8,236,061 B2 | 8/2012 | Heldreth et al. | |
| 8,366,782 B2 | 2/2013 | Wright | |
| 8,470,047 B2 | 6/2013 | Hazebrouck et al. | |
| 8,545,570 B2* | 10/2013 | Crabtree et al. | 623/20.24 |
| 8,556,985 B2 | 10/2013 | Meridew | |
| 8,591,594 B2* | 11/2013 | Parisi et al. | 623/20.32 |
| 8,603,101 B2* | 12/2013 | Claypool et al. | 606/102 |
| 8,617,250 B2* | 12/2013 | Metzger | 623/20.32 |
| 8,632,600 B2* | 1/2014 | Zannis et al. | 623/20.17 |
| 8,658,710 B2 | 2/2014 | McKellop et al. | |
| 8,715,359 B2 | 5/2014 | Deffenbaugh et al. | |
| 8,715,362 B2 | 5/2014 | Reiley et al. | |
| 8,727,203 B2 | 5/2014 | Wang et al. | |
| 8,900,321 B2 | 12/2014 | Weiss et al. | |
| 2001/0010023 A1 | 7/2001 | Schwartz et al. | |
| 2001/0047211 A1 | 11/2001 | Leclercq et al. | |
| 2002/0120274 A1 | 8/2002 | Overaker et al. | |
| 2002/0161448 A1 | 10/2002 | Hayes, Jr. et al. | |
| 2002/0173855 A1 | 11/2002 | Mansmann | |
| 2003/0004578 A1 | 1/2003 | Brown et al. | |
| 2003/0014122 A1 | 1/2003 | Whiteside | |
| 2003/0035747 A1 | 2/2003 | Anderson et al. | |
| 2003/0036801 A1 | 2/2003 | Schwartz et al. | |
| 2003/0044301 A1 | 3/2003 | Lefebvre et al. | |
| 2003/0050705 A1 | 3/2003 | Cueille et al. | |
| 2003/0075013 A1 | 4/2003 | Grohowski | |
| 2003/0139817 A1* | 7/2003 | Tuke et al. | 623/20.32 |
| 2003/0153981 A1 | 8/2003 | Wang et al. | |
| 2003/0171818 A1 | 9/2003 | Lewallen | |
| 2003/0171820 A1 | 9/2003 | Wilshaw et al. | |
| 2003/0212161 A1 | 11/2003 | McKellop et al. | |
| 2003/0220700 A1 | 11/2003 | Hammer et al. | |
| 2003/0225456 A1 | 12/2003 | Ek | |
| 2004/0015170 A1 | 1/2004 | Tallarida et al. | |
| 2004/0015770 A1 | 1/2004 | Kimoto | |
| 2004/0019384 A1 | 1/2004 | Kirking et al. | |
| 2004/0030397 A1 | 2/2004 | Collazo | |
| 2004/0039450 A1 | 2/2004 | Griner et al. | |
| 2004/0049284 A1 | 3/2004 | German et al. | |
| 2004/0102854 A1 | 5/2004 | Zhu | |
| 2004/0162620 A1 | 8/2004 | Wyss | |
| 2004/0167632 A1 | 8/2004 | Wen et al. | |
| 2004/0167633 A1 | 8/2004 | Wen et al. | |
| 2004/0186583 A1 | 9/2004 | Keller | |
| 2004/0186585 A1 | 9/2004 | Feiwell | |
| 2004/0199250 A1 | 10/2004 | Fell | |
| 2004/0215345 A1* | 10/2004 | Perrone et al. | 623/20.32 |
| 2004/0243237 A1 | 12/2004 | Unwin et al. | |
| 2005/0015153 A1 | 1/2005 | Goble et al. | |
| 2005/0021147 A1 | 1/2005 | Tarabichi | |
| 2005/0048193 A1 | 3/2005 | Li et al. | |
| 2005/0055102 A1 | 3/2005 | Tornier et al. | |
| 2005/0059750 A1 | 3/2005 | Sun et al. | |
| 2005/0064042 A1 | 3/2005 | Vunjak-Novakovic et al. | |
| 2005/0069629 A1 | 3/2005 | Becker et al. | |
| 2005/0100578 A1 | 5/2005 | Schmid et al. | |
| 2005/0107884 A1 | 5/2005 | Johnson et al. | |
| 2005/0107886 A1* | 5/2005 | Crabtree et al. | 623/20.24 |
| 2005/0112397 A1 | 5/2005 | Rolfe et al. | |
| 2005/0123672 A1 | 6/2005 | Justin et al. | |
| 2005/0125068 A1 | 6/2005 | Hozack et al. | |
| 2005/0192672 A1* | 9/2005 | Wyss et al. | 623/20.27 |
| 2005/0203631 A1* | 9/2005 | Daniels et al. | 623/20.32 |
| 2005/0209702 A1* | 9/2005 | Todd et al. | 623/20.33 |
| 2005/0249625 A1 | 11/2005 | Bram et al. | |
| 2006/0002810 A1 | 1/2006 | Grohowski, Jr. | |
| 2006/0015185 A1* | 1/2006 | Chambat et al. | 623/20.33 |
| 2006/0030945 A1 | 2/2006 | Wright | |
| 2006/0036329 A1 | 2/2006 | Webster et al. | |
| 2006/0047283 A1 | 3/2006 | Evans, III et al. | |
| 2006/0052875 A1* | 3/2006 | Bernero et al. | 623/20.33 |
| 2006/0100714 A1 | 5/2006 | Ensign | |
| 2006/0111790 A1 | 5/2006 | Dietz | |
| 2006/0136067 A1* | 6/2006 | Pendleton et al. | 623/20.34 |
| 2006/0163774 A1 | 7/2006 | Abels et al. | |
| 2006/0178749 A1 | 8/2006 | Pendleton et al. | |
| 2006/0195195 A1* | 8/2006 | Burstein et al. | 623/20.33 |
| 2006/0198943 A1 | 9/2006 | Kumar | |
| 2006/0224244 A1* | 10/2006 | Thomas et al. | 623/20.28 |
| 2006/0228247 A1 | 10/2006 | Grohowski | |
| 2006/0231402 A1 | 10/2006 | Clasen et al. | |
| 2006/0235537 A1 | 10/2006 | Kuczynski et al. | |
| 2006/0235542 A1 | 10/2006 | Hodorek et al. | |
| 2006/0241776 A1 | 10/2006 | Brown et al. | |
| 2006/0241781 A1 | 10/2006 | Brown et al. | |
| 2006/0257358 A1 | 11/2006 | Wen et al. | |
| 2006/0265079 A1* | 11/2006 | D'Alessio | 623/20.15 |
| 2006/0271191 A1 | 11/2006 | Hermansson | |
| 2006/0279908 A1 | 12/2006 | Omori et al. | |
| 2006/0289388 A1 | 12/2006 | Yang et al. | |
| 2007/0010890 A1 | 1/2007 | Collazo | |
| 2007/0061014 A1 | 3/2007 | Naegerl | |
| 2007/0073409 A1 | 3/2007 | Cooney, III et al. | |
| 2007/0078521 A1 | 4/2007 | Overholser et al. | |
| 2007/0100463 A1* | 5/2007 | Aram et al. | 623/20.29 |
| 2007/0129809 A1 | 6/2007 | Meridew et al. | |
| 2007/0142921 A1 | 6/2007 | Lewis et al. | |
| 2007/0162143 A1 | 7/2007 | Wasielewski | |
| 2007/0162144 A1 | 7/2007 | Wasielewski | |
| 2007/0172380 A1 | 7/2007 | Tatsumoto et al. | |
| 2007/0173948 A1 | 7/2007 | Meridew et al. | |
| 2007/0179628 A1 | 8/2007 | Rochetin | |
| 2007/0191962 A1 | 8/2007 | Jones et al. | |
| 2007/0196230 A1 | 8/2007 | Hamman et al. | |
| 2007/0203582 A1* | 8/2007 | Campbell | 623/20.34 |
| 2007/0219637 A1 | 9/2007 | Berelsman et al. | |
| 2007/0219639 A1 | 9/2007 | Otto et al. | |
| 2007/0255412 A1 | 11/2007 | Hajaj et al. | |
| 2007/0287027 A1 | 12/2007 | Justin et al. | |
| 2007/0293647 A1 | 12/2007 | McKellop et al. | |

(56) References Cited

U.S. PATENT DOCUMENTS

| | | | |
|---|---|---|---|
| 2008/0004708 A1* | 1/2008 | Wyss | 623/20.24 |
| 2008/0021567 A1 | 1/2008 | Meulink et al. | |
| 2008/0051908 A1* | 2/2008 | Angibaud et al. | 623/20.32 |
| 2008/0091271 A1 | 4/2008 | Bonitati et al. | |
| 2008/0091272 A1 | 4/2008 | Aram et al. | |
| 2008/0097616 A1 | 4/2008 | Meyers et al. | |
| 2008/0109081 A1 | 5/2008 | Bao et al. | |
| 2008/0114462 A1* | 5/2008 | Guidera et al. | 623/20.27 |
| 2008/0114464 A1* | 5/2008 | Barnett et al. | 623/20.33 |
| 2008/0119940 A1 | 5/2008 | Otto et al. | |
| 2008/0133019 A1 | 6/2008 | Andrysek | |
| 2008/0147187 A1 | 6/2008 | Bollinger et al. | |
| 2008/0161927 A1 | 7/2008 | Savage et al. | |
| 2008/0188855 A1 | 8/2008 | Brown et al. | |
| 2008/0188942 A1 | 8/2008 | Brown et al. | |
| 2008/0195108 A1 | 8/2008 | Bhatnagar et al. | |
| 2008/0199720 A1 | 8/2008 | Liu | |
| 2008/0206297 A1 | 8/2008 | Roeder et al. | |
| 2008/0215098 A1 | 9/2008 | Imwinkelried et al. | |
| 2009/0011384 A1 | 1/2009 | Collins et al. | |
| 2009/0018560 A1 | 1/2009 | Mayer et al. | |
| 2009/0048675 A1 | 2/2009 | Bhatnagar et al. | |
| 2009/0048680 A1 | 2/2009 | Naegerl | |
| 2009/0054985 A1 | 2/2009 | Anderson | |
| 2009/0082873 A1 | 3/2009 | Hazebrouck et al. | |
| 2009/0084491 A1 | 4/2009 | Uthgenannt et al. | |
| 2009/0088859 A1* | 4/2009 | Hazebrouck et al. | 623/20.14 |
| 2009/0088861 A1* | 4/2009 | Tuke et al. | 623/20.32 |
| 2009/0100190 A1 | 4/2009 | Besombe et al. | |
| 2009/0125114 A1 | 5/2009 | May et al. | |
| 2009/0125115 A1* | 5/2009 | Popoola et al. | 623/20.14 |
| 2009/0132055 A1 | 5/2009 | Ferro | |
| 2009/0149964 A1 | 6/2009 | May et al. | |
| 2009/0182433 A1 | 7/2009 | Reiley et al. | |
| 2009/0192610 A1 | 7/2009 | Case et al. | |
| 2009/0204222 A1* | 8/2009 | Burstein et al. | 623/20.34 |
| 2009/0210067 A1 | 8/2009 | Meridew | |
| 2009/0216325 A1 | 8/2009 | May et al. | |
| 2009/0264894 A1 | 10/2009 | Wasielewski | |
| 2009/0265011 A1* | 10/2009 | Mandell | 623/20.15 |
| 2009/0265012 A1 | 10/2009 | Engh et al. | |
| 2009/0265013 A1 | 10/2009 | Mandell | |
| 2009/0292365 A1 | 11/2009 | Smith et al. | |
| 2009/0295035 A1 | 12/2009 | Evans | |
| 2009/0326663 A1 | 12/2009 | Dun | |
| 2009/0326664 A1 | 12/2009 | Wagner et al. | |
| 2009/0326665 A1 | 12/2009 | Wyss et al. | |
| 2009/0326666 A1 | 12/2009 | Wyss et al. | |
| 2009/0326667 A1 | 12/2009 | Williams et al. | |
| 2009/0326674 A1 | 12/2009 | Liu et al. | |
| 2010/0016979 A1 | 1/2010 | Wyss et al. | |
| 2010/0036499 A1 | 2/2010 | Pinskerova | |
| 2010/0036500 A1 | 2/2010 | Heldreth et al. | |
| 2010/0042224 A1 | 2/2010 | Otto et al. | |
| 2010/0042225 A1 | 2/2010 | Shur | |
| 2010/0057217 A1 | 3/2010 | Breimesser et al. | |
| 2010/0063594 A1 | 3/2010 | Hazebrouck et al. | |
| 2010/0070045 A1 | 3/2010 | Ek | |
| 2010/0076563 A1 | 3/2010 | Otto et al. | |
| 2010/0076564 A1 | 3/2010 | Schilling et al. | |
| 2010/0076569 A1 | 3/2010 | Langhorn | |
| 2010/0094420 A1 | 4/2010 | Grohowski, Jr. | |
| 2010/0094429 A1 | 4/2010 | Otto | |
| 2010/0098574 A1 | 4/2010 | Liu et al. | |
| 2010/0100189 A1 | 4/2010 | Metzger | |
| 2010/0100190 A1 | 4/2010 | May et al. | |
| 2010/0100191 A1 | 4/2010 | May et al. | |
| 2010/0114322 A1 | 5/2010 | Clifford et al. | |
| 2010/0125337 A1 | 5/2010 | Grecco et al. | |
| 2010/0145393 A1 | 6/2010 | Fallin et al. | |
| 2010/0161067 A1 | 6/2010 | Saleh et al. | |
| 2010/0191341 A1 | 7/2010 | Byrd | |
| 2010/0222890 A1* | 9/2010 | Barnett et al. | 623/20.33 |
| 2010/0256771 A1 | 10/2010 | Roberts et al. | |
| 2010/0262144 A1 | 10/2010 | Kelman et al. | |
| 2010/0262253 A1* | 10/2010 | Cipolletti et al. | 623/20.28 |
| 2010/0286788 A1 | 11/2010 | Komistek | |
| 2010/0292804 A1 | 11/2010 | Samuelson | |
| 2010/0305710 A1 | 12/2010 | Metzger et al. | |
| 2010/0312350 A1 | 12/2010 | Bonutti | |
| 2011/0009974 A1 | 1/2011 | Blaylock et al. | |
| 2011/0029090 A1* | 2/2011 | Zannis et al. | 623/20.28 |
| 2011/0029092 A1* | 2/2011 | Deruntz et al. | 623/20.32 |
| 2011/0035013 A1 | 2/2011 | Winslow et al. | |
| 2011/0035017 A1* | 2/2011 | Deffenbaugh et al. | 623/20.14 |
| 2011/0035018 A1 | 2/2011 | Deffenbaugh et al. | 623/20.28 |
| 2011/0046735 A1* | 2/2011 | Metzger et al. | 623/14.12 |
| 2011/0071642 A1 | 3/2011 | Moussa | |
| 2011/0106268 A1* | 5/2011 | Deffenbaugh et al. | 623/20.32 |
| 2011/0178605 A1* | 7/2011 | Auger et al. | 623/20.15 |
| 2011/0178606 A1 | 7/2011 | Deffenbaugh et al. | |
| 2011/0190897 A1* | 8/2011 | Guidera et al. | 623/20.27 |
| 2012/0022660 A1* | 1/2012 | Wentorf | 623/20.32 |
| 2012/0067853 A1 | 3/2012 | Wang et al. | |
| 2012/0116527 A1 | 5/2012 | Birkbeck et al. | |
| 2012/0185053 A1 | 7/2012 | Berger | |
| 2012/0296438 A1* | 11/2012 | Metzger et al. | 623/20.29 |
| 2012/0303122 A1* | 11/2012 | Servidio | 623/14.12 |
| 2012/0323333 A1* | 12/2012 | Metzger | 623/20.32 |
| 2013/0020733 A1 | 1/2013 | Berger | |
| 2013/0022943 A1 | 1/2013 | Collins et al. | |
| 2013/0024001 A1* | 1/2013 | Wentorf et al. | 623/20.32 |
| 2013/0066437 A1 | 3/2013 | Weeden | |
| 2013/0079885 A1* | 3/2013 | Meier | A61F 2/38 623/20.21 |
| 2013/0131818 A1* | 5/2013 | Parisi et al. | 623/20.31 |
| 2013/0173009 A1* | 7/2013 | Hershberger | 623/20.29 |
| 2013/0184829 A1* | 7/2013 | Wyss | A61F 2/38 623/20.28 |
| 2013/0184830 A1 | 7/2013 | Hazebrouck et al. | |
| 2013/0218284 A1 | 8/2013 | Eickmann et al. | |
| 2013/0304222 A1* | 11/2013 | Liu et al. | 623/20.33 |
| 2013/0310945 A1 | 11/2013 | Slone et al. | |
| 2014/0025176 A1* | 1/2014 | Wentorf et al. | 623/20.32 |
| 2014/0052269 A1* | 2/2014 | Claypool et al. | 623/20.33 |
| 2014/0081412 A1* | 3/2014 | Metzger | 623/20.33 |
| 2014/0172112 A1 | 6/2014 | Marter | |
| 2014/0277517 A1 | 9/2014 | Winslow | |
| 2014/0277529 A1 | 9/2014 | Stalcup et al. | |
| 2014/0277539 A1 | 9/2014 | Cook et al. | |
| 2014/0277544 A1 | 9/2014 | Viscogliosi et al. | |

FOREIGN PATENT DOCUMENTS

| | | |
|---|---|---|
| CN | 101068503 A | 11/2007 |
| CN | 101405039 A | 4/2009 |
| CN | 101411649 A | 4/2009 |
| DE | 4308563 A1 | 9/1994 |
| DE | 102006005034 A1 | 8/2007 |
| EP | 0063632 A1 | 11/1982 |
| EP | 0495340 A1 | 7/1992 |
| EP | 0634156 A2 | 1/1995 |
| EP | 0636352 A2 | 2/1995 |
| EP | 0732092 A2 | 9/1996 |
| EP | 0765645 A2 | 4/1997 |
| EP | 1186277 A2 | 3/2002 |
| EP | 1226799 A1 | 7/2002 |
| EP | 1421918 A1 | 5/2004 |
| EP | 1779812 A1 | 5/2007 |
| EP | 1923079 A1 | 5/2008 |
| FR | 2653992 A1 | 5/1991 |
| FR | 2780636 A1 | 1/2000 |
| FR | 2837093 A1 | 9/2003 |
| GB | 1065354 A | 4/1967 |
| GB | 2293109 A | 3/1996 |
| WO | 9524874 A1 | 9/1995 |
| WO | 9530388 A1 | 11/1995 |
| WO | 9624302 A1 | 8/1996 |
| WO | 9624304 A1 | 8/1996 |
| WO | 9725942 A1 | 7/1997 |
| WO | 9966864 A1 | 12/1999 |
| WO | 0074554 A1 | 12/2000 |
| WO | 03039609 A1 | 5/2003 |
| WO | 03101647 A2 | 12/2003 |

(56) References Cited

FOREIGN PATENT DOCUMENTS

| WO | 2005009489 A2 | 2/2005 |
| WO | 2005009729 A2 | 2/2005 |
| WO | 2006005150 A1 | 1/2006 |
| WO | 2006014294 A1 | 2/2006 |
| WO | 2006079459 A1 | 8/2006 |
| WO | 2006130350 A2 | 12/2006 |
| WO | 2007053572 A2 | 5/2007 |
| WO | 2008048820 A2 | 4/2008 |
| WO | 2009046212 A2 | 4/2009 |
| WO | 2009128943 A2 | 10/2009 |
| WO | 2009143420 A2 | 11/2009 |
| WO | 2010056962 A1 | 5/2010 |

OTHER PUBLICATIONS

DePuy Inc., "AMK Total Knee System Product Brochure", 1996, 8 pages.

DePuy Orthopaedics, Inc., "AMK Total Knee System Legend II Surgical Technique", 1998, 30 pages.

General Plastics Manufacturing Company, "Last-A-Foam®," FR-6700 Series Product Sheet, 2000, 6 pages.

General Plastics Manufacturing Company, "Tooling Board Specifications," FR-4500® Series Specification Sheet, 2002, 2 pages.

General Plastics Manufacturing Company, "Tooling Boards," FR-4500® Series Product Data Sheet, 2002, 4 pages.

A. Harvey et al., "Factors Affecting the Range of Movement of Total Knee Arthoplasty," The Journal of Bone and Joint Surgery, vol. 75-B, No. 6, Nov. 1993, pp. 950-955.

Media Cybernetics, Inc., "Image-Pro Plus: Powerful and Customizable Image Processing and Analysis Software for Industrial Applications," 2009, 8 pages.

Signus Medizintechnik, "Peek-Optima®, The Polymer for Implants, Technical Information for the Medical Professional", 7 pages, printed from http://old.arid.cz/SIG_opt1.htm, on Aug. 18, 2009.

J. Shaw et al., "The Longitudinal Axis of the Knee and the Role of the Cruciate Ligaments in Controlling Transverse Rotation," The Journal of Bone & Joint Surgery, vol. 56-A, No. 8, Dec. 1974, pp. 1603-1609.

Thackray Orthopaedic, "Second International Johnson-Elloy Knee Meeting," Mar. 1987, 9 pages.

Thackray Orthopaedic, "Johnson Elloy Knee System: Operative Technique", 1988, 34 pages.

Zimmer, Nexgen Trabecular Metal Tibial Tray, "The Best Thing Next to Bone," 97-5954-001-00, 2007, 4 pages.

Zimmer, Trabecular Metal Monoblock Tibial Components, An Optimal Combination of Material and Design, www.zimmer.com, 2009, 3 pages.

Partial European Search Report for European Patent Application No. 09170648.1-1269, Jan. 13, 2010, 6 pages.

European Search Report for European Patent Application No. 09170648.1-1269, Mar. 5, 2010, 15 pages.

Partial European Search Report for European Patent Application No. 08164944.4-2310, Dec. 15, 2008, 6 pages.

European Search Report for European Patent Application No. 08164944.4-2310, Mar. 16, 2009, 12 pages.

European Search Report for European Patent Application No. 08253140.1-2310, Dec. 23, 2008, 8 pages.

European Search Report for European Patent Application No. 10188962.4-2310, Mar. 2, 2011, 7 pages.

European Search Report for European Patent Application No. 10188963.2.2310, Mar. 1, 2011, 6 pages.

European Search Report for European Patent Application No. 10189698.3-2310, Feb. 23, 2011, 4 pages.

Specification as filed in U.S. Appl. No. 12/691,280, filed Jan. 21, 2010, 35 Pages.

Non-Final Office Action for U.S. Appl. No. 12/691,280, dated Mar. 29, 2011, 10 Pages.

Specification as filed for U.S. Appl. No. 12/894,651, filed Sep. 30, 2010, 29 Pages.

\* cited by examiner

US 9,398,956 B2

FIXED-BEARING KNEE PROSTHESIS HAVING INTERCHANGEABLE COMPONENTS

This application is a continuation of copending U.S. patent application Ser. No. 12/904,614 filed Oct. 14, 2010, which is a continuation-in-part of U.S. Pat. No. 8,128,703 filed on Nov. 17, 2009, which is a continuation-in-part of U.S. Pat. No. 7,628,818 filed on Sep. 28, 2007. The entirety of each of those applications is expressly incorporated herein by reference.

TECHNICAL FIELD

The present disclosure relates generally to an implantable orthopaedic prosthesis, and more particularly to an implantable knee prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a knee replacement procedure, a tibial tray is implanted into the patient's tibia. A bearing is secured to the tibial tray. The condyle surfaces of a replacement femoral component bear against the tibial bearing.

One type of knee prosthesis is a fixed-bearing knee prosthesis. As its name suggests, the bearing of a fixed-bearing knee prosthesis does not move relative to the tibial tray. Fixed-bearing designs are commonly used when the condition of the patient's soft tissue (i.e., knee ligaments) does not allow for the use of a knee prosthesis having a mobile bearing.

The components of a fixed-bearing knee prosthesis are typically provided by the manufacturer in matching sizes. Specifically, most currently available fixed-bearing knee prostheses allow the surgeon to use a number of bearing sizes for a particular size of femoral component, but each bearing size is generally matched to a particular size of tibial tray.

SUMMARY

According to one aspect, a fixed-bearing knee prosthesis includes a femoral component having a medial condyle surface and a lateral condyle surface. The prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. The platform has a posterior buttress extending along a posterior section of a perimeter of the platform and extending upwardly from an upper surface of the platform. An anterior buttress extends along an anterior section of the perimeter of the platform and upwardly from the upper surface of the platform. The tibial tray also has an elongated bore that opens into the upper surface of the posterior buttress.

The posterior buttress is generally Y-shaped and has a first arm extending along a posterior edge of the platform and having a first undercut defined therein. A second arm extends along the posterior edge of the platform in a direction away from the first arm and has a second undercut defined therein. A third arm extends anteriorly away from the first arm and the second arm.

A first imaginary line extends along a lateral-most edge of the first arm, with a second imaginary line extending along a medial-most edge of the second arm and intersecting the first imaginary line to define an angle of intersection therebetween.

In some illustrative embodiments, the angle of intersection of the imaginary lines is between 45-145°. In some illustrative embodiments, the angle of intersection of the imaginary lines is between 60-120°. In a specific illustrative embodiment, the angle of intersection of the imaginary lines is approximately 90°.

In some illustrative embodiments, the anterior buttress is generally T-shaped. In such cases, the anterior buttress includes a first arm extending along an anterior edge of the platform with a first undercut defined therein, and a second arm extending along the anterior edge of the platform in a direction away from the first arm and with a second undercut defined therein. A third arm extends posteriorly away from the first arm and the second arm.

The third arm of the posterior buttress may be contiguous with the third arm of the anterior buttress.

The bearing may include a first posterior tab positioned in the first undercut defined in the first arm of the posterior buttress, a second posterior tab positioned in the second undercut defined in the second arm of the posterior buttress, a first anterior tab positioned in the first undercut defined in the first arm of the anterior buttress, and a second anterior tab positioned in the second undercut defined in the second arm of the anterior buttress.

Both the medial bearing surface and the lateral bearing surface are defined in the upper surface of the bearing. The lower surface of the bearing contacts the upper surface of the platform and includes a posterior recess and an anterior recess formed therein. The posterior buttress is positioned in the posterior recess and the anterior buttress is positioned in the anterior recess. The posterior recess may be contiguous with the anterior recess.

According to another aspect, a fixed-bearing knee prosthesis includes a femoral component having a medial condyle surface and a lateral condyle surface. The prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. The platform has a posterior buttress extending along a posterior section of a perimeter of the platform and extending upwardly from an upper surface of the platform. An anterior buttress extends along an anterior section of the perimeter of the platform and upwardly from the upper surface of the platform. The tibial tray also has an elongated bore that opens into the upper surface of the posterior buttress.

The posterior buttress is generally Y-shaped and has a first arm extending along a posterior edge of the platform with a first undercut defined therein, and a second arm extending along the posterior edge of the platform in a direction away from the first arm with a second undercut defined therein. A third arm extends anteriorly away from the first arm and the second arm.

The anterior buttress includes a first arm extending along an anterior edge of the platform with a first undercut defined therein. A second arm of the anterior buttress extends along the anterior edge of the platform in a direction away from the first arm of the anterior buttress with a second undercut defined therein.

A first imaginary line extends along a posterior-most edge of the first arm of the anterior buttress and a posterior-most edge of the second arm of the anterior buttress. A second imaginary line extends along the longitudinal axis of the third arm of the posterior buttress and intersects the first imaginary line to define an angle of intersection therebetween. The angle of intersection is approximately 90°.

The anterior buttress may include a third arm extending posteriorly away from the first arm and the second arm in a direction parallel to the second imaginary line. The third arm of the posterior buttress may be contiguous with the third arm of the anterior buttress.

The bearing may include a first posterior tab positioned in the first undercut defined in the first arm of the posterior buttress, a second posterior tab positioned in the second undercut defined in the second arm of the posterior buttress, a first anterior tab positioned in the first undercut defined in the first arm of the anterior buttress, and a second anterior tab positioned in the second undercut defined in the second arm of the anterior buttress.

Both the medial bearing surface and the lateral bearing surface are defined in the upper surface of the bearing. The lower surface of the bearing contacts the upper surface of the platform and includes a posterior recess and an anterior recess formed therein. The posterior buttress is positioned in the posterior recess and the anterior buttress is positioned in the anterior recess. The posterior recess may be contiguous with the anterior recess.

According to another aspect, a fixed-bearing knee prosthesis includes a femoral component having a medial condyle surface and a lateral condyle surface, and a tibial tray having a platform with an elongated stem extending downwardly from a lower surface thereof. The platform has a generally Y-shaped posterior buttress extending upwardly from an upper surface of the platform. A pair of arms of the posterior buttress extend along a posterior section of a perimeter of the platform. Each of the pair of arms has an undercut defined therein. The platform also has an anterior buttress extending along an anterior section of the perimeter of the platform and extending upwardly from the upper surface of the platform. The knee prosthesis also includes a plurality of bearings configured to be secured to the tibial tray. Each of the plurality of bearings has a width that is different from at least some of the other of the plurality of bearings. Each of the plurality of bearings also has an upper surface having a medial bearing surface configured to articulate with the medial condyle surface of the femoral component and a lateral bearing surface configured to articulate with the lateral condyle surface of the femoral component. A lower surface of each of the plurality of bearings has at least one recess defined therein to receive the posterior buttress and the anterior buttress. Each of the plurality of bearings also includes a pair of posterior tabs arranged to be respectively received in the undercuts defined in the pair of arms of the posterior buttress. The tibial tray also has an elongated bore that opens into the upper surface of the posterior buttress.

The recess of the bearing may define a single, contiguous recess that receives both the posterior buttress and the anterior buttress.

The anterior buttress may be generally T-shaped with a pair of arms extending along an anterior edge of the platform. Each of the pair of arms of the anterior buttress may have an undercut defined therein. Each of the plurality of bearings may further include a pair of anterior tabs arranged to be respectively received in the undercuts defined in the pair of arms of the anterior buttress.

The posterior buttress may be contiguous with the anterior buttress.

BRIEF DESCRIPTION OF THE DRAWINGS

The detailed description particularly refers to the following figures, in which.

DETAILED DESCRIPTION OF THE DRAWINGS

Figure 1:
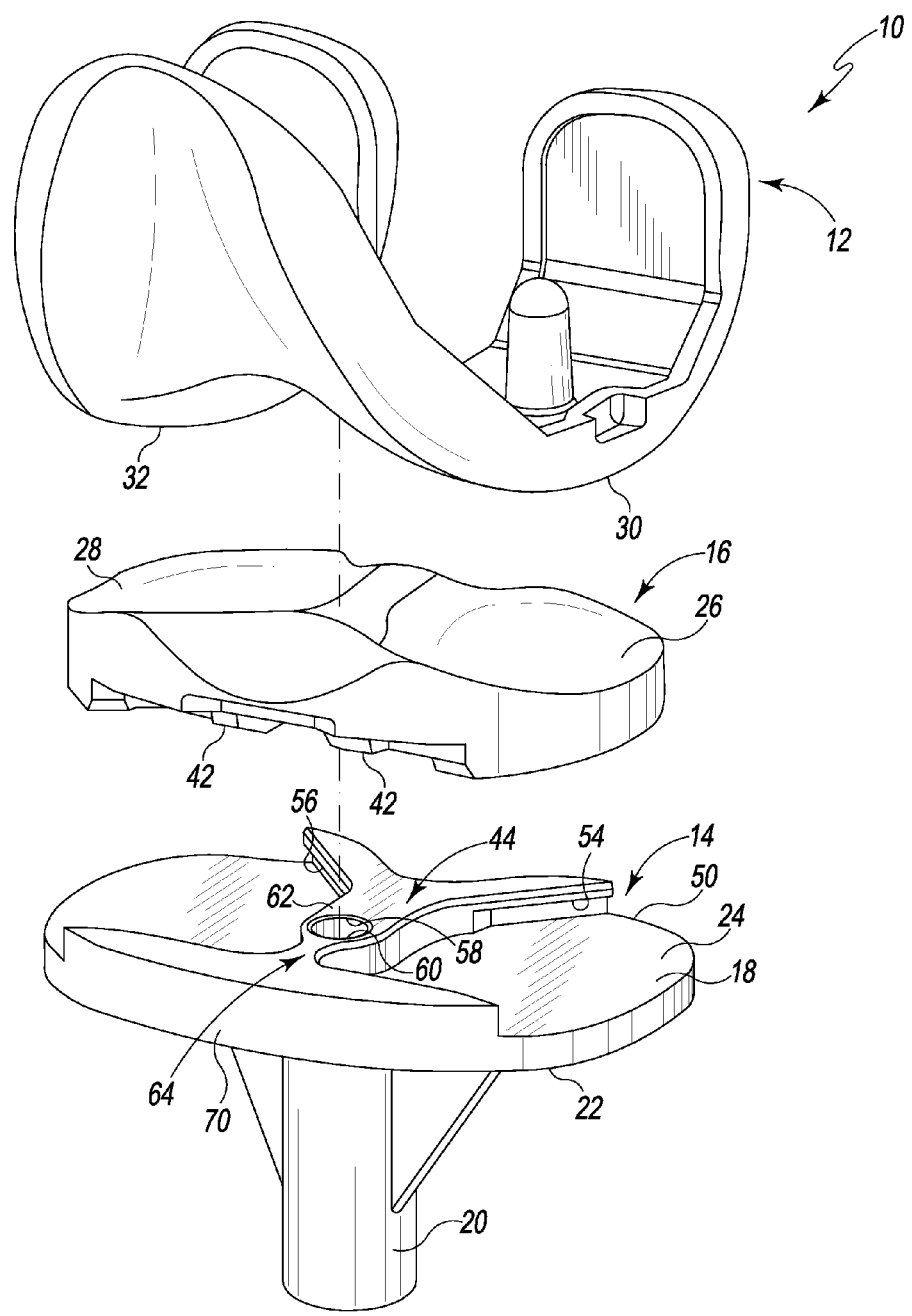
FIG. 1 is an exploded perspective view of a fixed-bearing knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-4, there is shown a fixed-bearing knee prosthesis 10. The knee prosthesis 10 includes a femoral component 12, a tibial tray 14, and a bearing 16. The tibial tray 14 includes a platform 18 having a fixation member, such as an elongated stem 20, extending away from its lower surface 22. The elongated tibial stem 20 is configured to be implanted into a surgically prepared end of a patient's tibia (not shown). It should be appreciated that other fixation members, such as one or more short pegs or posts, may be used in lieu of the elongated stem 20. The bearing 16 is securable to the tibial tray 14. In particular, as will be discussed below in greater detail, the bearing 16 may be snap-fit to the tibial tray 14. In such a way, the bearing 16 is fixed relative to the tibial tray 14 (i.e., it is not rotatable or moveable in the anterior/posterior or medial/lateral directions).

The bearing 16 includes a lateral bearing surface 26 and a medial bearing surface 28. The bearing surfaces 26, 28 are configured to articulate with a lateral condyle surface 30 and a medial condyle surface 32, respectively, of the femoral component 12. Specifically, the femoral component 12 is configured to be implanted into a surgically prepared end of the patient's femur (not shown), and is configured to emulate the configuration of the patient's natural femoral condyles. As such, the lateral condyle surface 30 and the medial condyle surface 32 are configured (e.g., curved) in a manner which mimics the condyles of the natural femur. The lateral condyle surface 30 and the medial condyle surface 32 are spaced apart from one another thereby defining an intercondylar notch therebetween.

The components of the knee prosthesis 10 that engage the natural bone, such as the femoral component 12 and the tibial tray 14, may be constructed with a biocompatible metal, such as a cobalt chrome alloy, although other materials may also be used. The bone engaging surfaces of these components may be textured to facilitate cementing the component to the bone. Such surfaces may also be porous coated to promote bone ingrowth for permanent fixation.

The bearing 16 may be constructed with a material that allows for smooth articulation between the bearing 16 and the femoral component 12, such as a polymeric material. One such polymeric material is polyethylene such as ultrahigh molecular weight polyethylene (UHMWPE).

Figure 2:
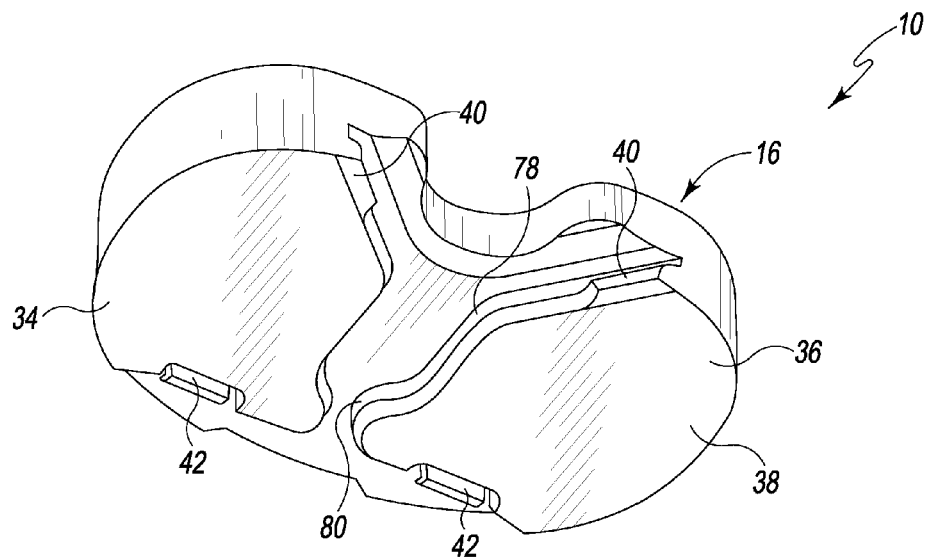
FIG. 2 is a bottom perspective view of the bearing of the knee prosthesis of FIG. 1.

As shown in FIG. 2, the lower surface 36 of the bearing 16 includes a lateral pedestal 34 and a medial pedestal 38. The pedestals 34, 38 have a number of posterior tabs 40 defined therein. A number of anterior tabs 42 are also defined in the bearing 16.

Figure 3:
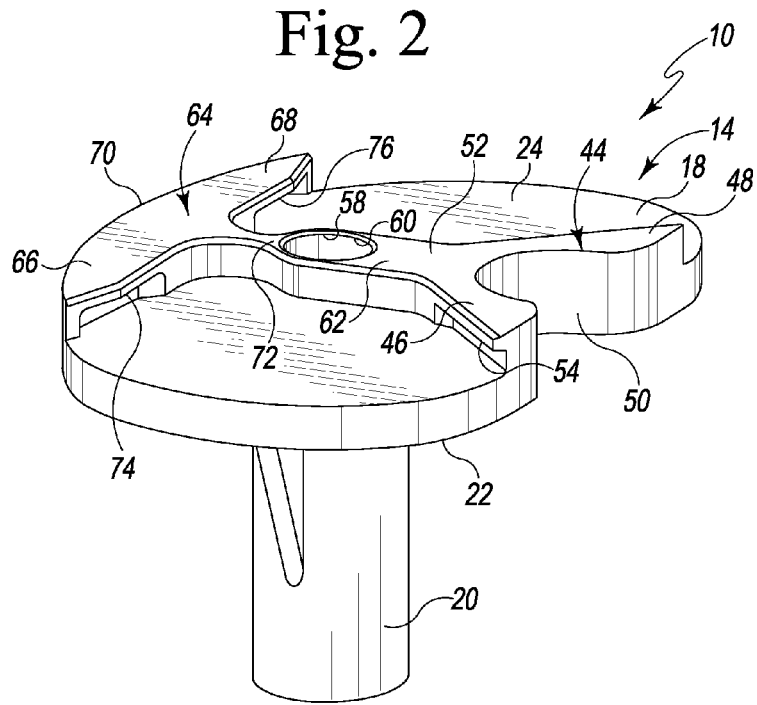
FIG. 3 is a perspective view of the tibial tray of the knee prosthesis of FIG. 1.
Figure 4:
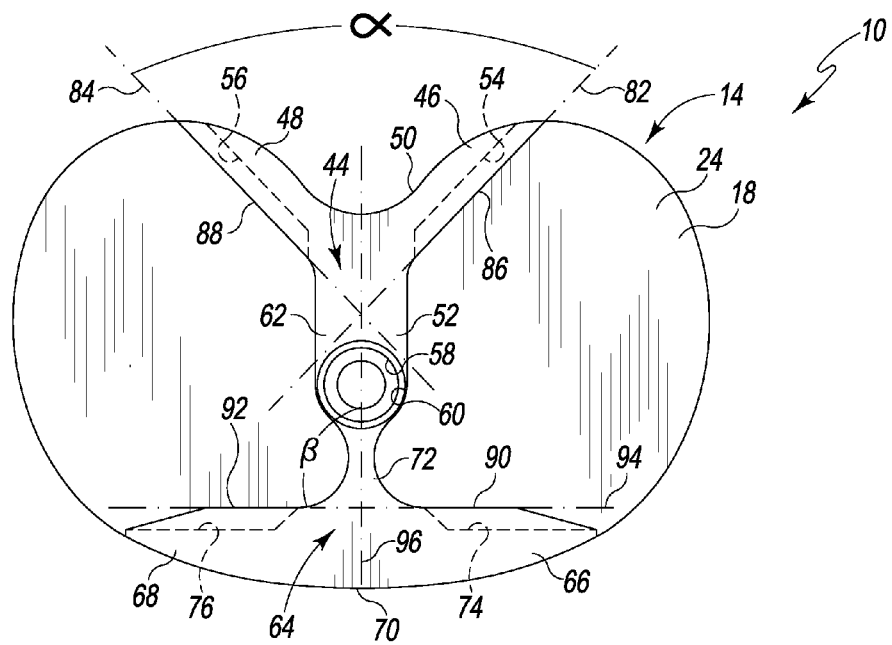
FIG. 4 is a plan view of the tibial tray of the knee prosthesis of FIG. 1.

As shown in FIGS. 3 and 4, a generally Y-shaped posterior buttress 44 extends upwardly from the upper surface 24 of the tibial tray 14. In the illustrative embodiment described herein, the posterior buttress 44 has a pair of arms 46, 48 extending along a posterior section of the perimeter of tibial tray's platform 18. Specifically, the lateral arm 46 of the posterior buttress 44 extends along the posterior edge 50 on the lateral side of the platform 18, whereas the medial arm 48 of the posterior buttress 44 extends along the posterior edge 50 on the medial side of the platform 18 in a direction away from the lateral arm 46. A third arm 52 of the posterior buttress 44 extends anteriorly away from the intersection of the lateral arm 46 and the medial arm 48 (i.e., in a direction toward the center of the platform 18).

The posterior buttress 44 has a pair of undercuts 54, 56 defined therein. Specifically, the lateral undercut 54 is defined in the lateral arm 46 of the posterior buttress 44, with the medial undercut 56 being defined in the medial arm 48 of the posterior buttress 44.

As can be seen in FIGS. 1, 3-10, and 12-14, the tibial tray 14 has an elongated bore 58 formed therein. A superior end 60 of the elongated bore 58 opens into the upper surface 62 of the posterior buttress 44. In the illustrative embodiments shown in FIGS. 9, 10, and 12-14, the superior end 60 of the elongated bore 58 opens into the third arm 52 of the posterior buttress 44. More particularly, in such illustrative embodiments, the superior end 60 of the elongated bore 58 opens into the anterior end of the third arm 52 of the posterior buttress 44. This is shown geometrically in FIGS. 9 and 13 in which an imaginary line 114 extending in the medial/lateral direction bisects the third arm 52 into an anterior half 116 and a posterior half 118. The superior end 60 of the elongated bore 58 opens into the anterior end of the third arm 52 of the posterior buttress 44 at a location in its anterior half 116.

Figure 12:
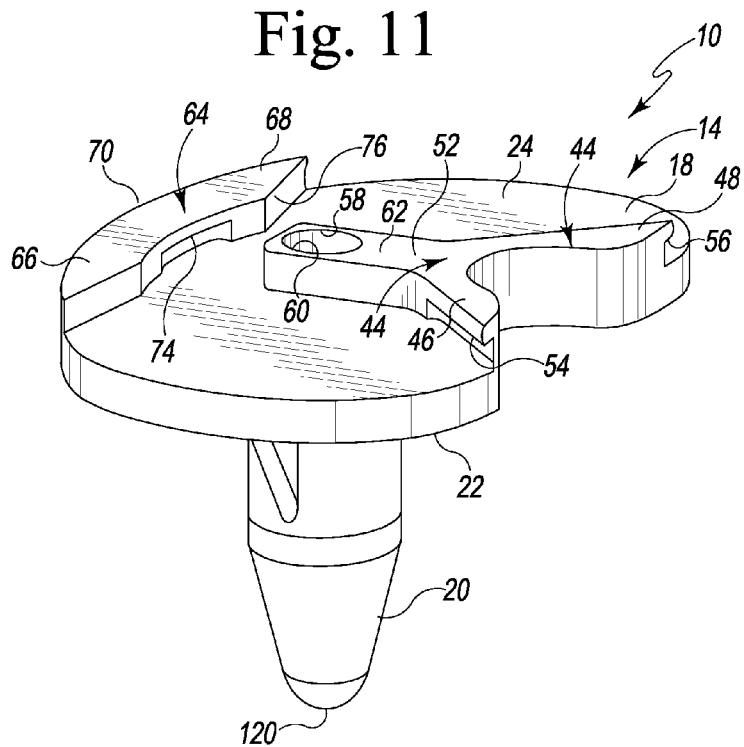

As can be seen best in FIG. 12, the elongated bore 58 extends in the superior/inferior direction. As a result, the elongated bore 58 extends away from its superior end 60 in the direction toward the distal end 120 of the tibial tray's elongated stem 20.

As also shown in FIGS. 3 and 4, a generally T-shaped anterior buttress 64 extends upwardly from the upper surface 24 of the tibial tray 14. In the illustrative embodiment described herein, the anterior buttress 64 has a pair of arms 66, 68 extending along an anterior section of the perimeter of tibial tray's platform 18. Specifically, the lateral arm 66 of the anterior buttress 64 extends along the anterior edge 70 on the lateral side of the platform 18, whereas the medial arm 68 of the anterior buttress 64 extends along the anterior edge 70 on the medial side of the platform 18 in a direction away from the lateral arm 66. A third arm 72 of the anterior buttress 64 extends posteriorly away from the intersection of the lateral arm 66 and the medial arm 68 (i.e., in a direction toward the center of the platform 18).

The anterior buttress 64 has a pair of undercuts 74, 76 defined therein. Specifically, the lateral undercut 74 is defined in the lateral arm 66 of the anterior buttress 64, with the medial undercut 76 being defined in the medial arm 68 of the anterior buttress 64.

In the illustrative embodiment of FIGS. 1-4, the posterior buttress 44 of the tibial tray 14 is contiguous with the tray's anterior buttress 64. Specifically, as shown in FIG. 4, the third arm 52 of the posterior buttress 44 is contiguous with the third arm 72 of the anterior buttress 64. However, as will be discussed below in greater detail, other embodiments are contemplated, including arrangements in which the buttresses are not contiguous. Moreover, the two buttresses 44, 64 are herein described as being of a similar height, although the buttresses could be embodied has having dissimilar heights.

To secure the tibial bearing 16 to the tibial tray 14, the posterior tabs 40 of the bearing 16 are positioned in the posterior undercuts 54, 56 of the tibial tray 14. Thereafter, the anterior portion of the tibial bearing 16 is advanced downwardly toward the tibial tray 14 such that the anterior tabs 42 of the tibial bearing 16 are deflected by the anterior buttress 64 and thereafter snapped into the anterior undercuts 74, 76 of the anterior buttress thereby securing the bearing 16 to the tray 14.

As the anterior portion of the bearing 16 is advanced downwardly in such a manner, the buttresses 44, 64 of the tibial tray 14 are captured between the pedestals 34, 38 of the bearing's lower surface 36. Specifically, the lower surface 36 of the bearing 16 has a posterior recess 78 and an anterior recess 80 defined therein. The posterior recess 78 is configured to compliment the shape of the posterior buttress 44 of the tibial tray 14. That is, when the bearing 16 is secured to the tibial tray 14, the sidewalls of the pedestals 34, 38 which define the posterior recess 78 contact the edges of the posterior buttress 44. Likewise, the anterior recess 80 is configured to compliment the shape of the anterior buttress 64 of the tibial tray 14—i.e., when the bearing 16 is secured to the tibial tray 14, the sidewalls of the pedestals 34, 38 which define the anterior recess 80 contact the edges of the anterior buttress 64. The dimensions of the recesses 78, 80 and the buttresses 44, 64 are selected such that a relatively tight fit is achieved. In such a way, the bearing 16 is fixed relative to the tibial tray 14. In particular, the configuration of the buttresses 44, 46 and the pedestals 34, 38 formed in the lower surface 36 of the bearing 16 prevent movement of the bearing 16 relative the tibial tray 14 in the anterior/posterior direction and the medial/lateral direction. Moreover, the posterior tabs positioned in the undercuts 54, 56 and the anterior tabs 42 positioned in the undercuts 74, 76 prevent lift off of the bearing 16 from the tibial tray 14. Rotational micromotion is reduced, if not prevented all together, by the relatively tight fit of the buttresses 44, 64 of the tibial tray 14 into the recesses 78, 80 of the bearing 16—particularly along the third arm 52 of the posterior buttress 44 and/or the third arm 72 of the anterior buttress 64.

As alluded to above, in the illustrative embodiment described herein, the posterior buttress 44 is embodied as a generally Y-shaped structure having a pair of arms 46, 48 extending in opposite directions along the posterior edge 50 of the tray's platform 18, with a third arm 52 extending anteriorly from the posterior edge 50 of the tibial tray 14 (i.e., in a direction toward the center of the tray's platform 18). As shown in FIG. 4, the lateral arm 46 of the posterior buttress 44 includes a lateral-most edge 86, whereas the medial arm 48 of the posterior buttress 44 has a medial-most edge 88. An imaginary line 82 extends along the lateral-most edge 86 and intersects an imaginary line 84 that extends along the medial-most edge 88 to define an angle of intersection (α). In the exemplary embodiments described herein, the angle of intersection (α) is between 45-145°. In more specific illustrative embodiments, the angle of intersection (α) is between 60-120°. In one such specific illustrative embodiment, the angle of intersection (α) is approximately 90°. Examples of such illustrative embodiments of the posterior buttress 44 are shown in FIGS. 6-9.

It should be appreciated that increasing the angle of intersection (α) reduces micromotion, while decreasing the angle of intersection (α) increases the load bearing surface area of the tibial tray 14. Although other configurations may be utilized, it has been found that arranging the arms 46, 48 of the posterior buttress 44 as described above (i.e., having an angle of intersection (α) between 60-120°) provides an unexpectedly beneficial working balance between these two considerations. On particularly well-balanced arrangement of the posterior buttress 44 is found in the illustrative embodiment where the angle of intersection (α) is approximately 90°.

As alluded to above, in the illustrative embodiment described herein, the anterior buttress 64 is embodied as a generally T-shaped structure having a pair of arms 66, 68 extending in opposite directions along the anterior edge 70 of the tray's platform 18, with a third arm 64 extending posteriorly from the anterior edge 70 of the tibial tray 14 (i.e., in a direction toward the center of the tray's platform 18). As shown in FIG. 4, the lateral arm 66 of the anterior buttress 64 includes a posterior-most edge 90, whereas the medial arm 68 of the anterior buttress 64 has a posterior-most edge 92. An imaginary line 94 extends along both the posterior-most edge 90 of the lateral arm 66 and the posterior-most edge 92 of the medial arm 68. An imaginary center line 96 extends along a longitudinal axis of the third arm 52 of the posterior buttress 44. As shown in FIG. 4, the imaginary center line 96 bisects the third arm 52 of the posterior buttress 44. The imaginary line 94 extending along the posterior-most edges 90, 92 of the arms 66, 68 of the anterior buttress 64 intersects the imaginary center line 96 extending along the longitudinal axis of the third arm 52 of the posterior buttress 44 to define an angle of intersection (β). In the illustrative embodiments described herein, the arms 66, 68 (and hence the undercuts 74, 76) of the anterior buttress 64 are configured to extend in the medial/lateral direction. As a result, in the illustrative embodiments described herein, the angle of intersection (β) is approximately 90°. As shown in FIGS. 6-9, such is the case throughout numerous illustrative embodiments of the anterior buttress 64.

Figure 5:
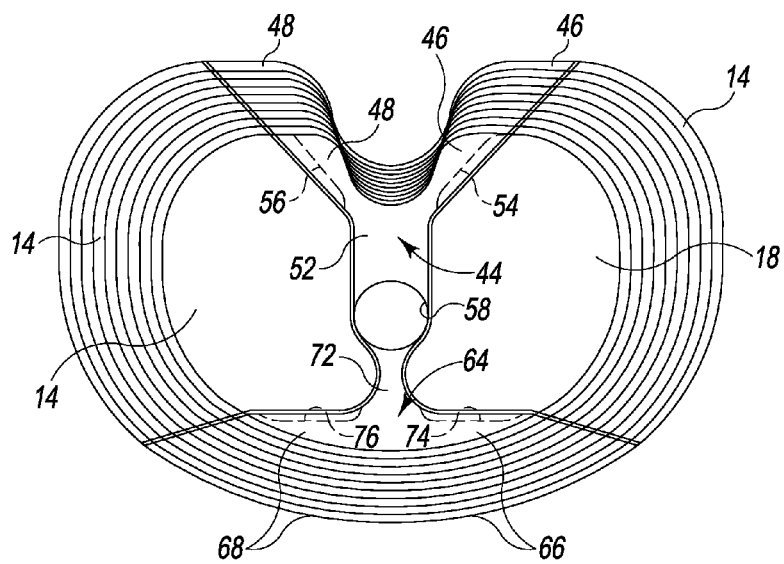
FIG. 5 is a diagrammatic plan view of a number of differently sized tibial trays of the knee prosthesis of FIG. 1.
Figure 6:
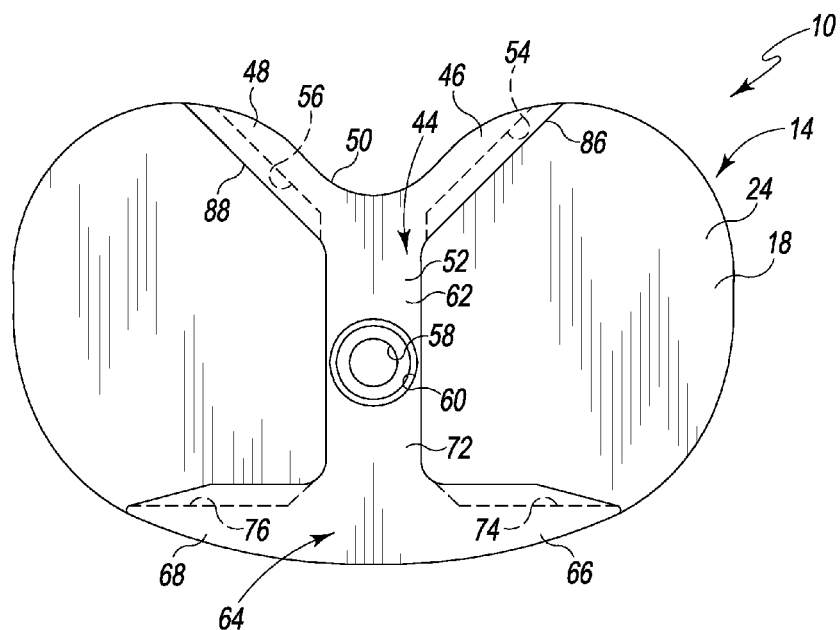
FIGS. 6-9 are similar to FIG. 4, but showing different embodiments of the tibial tray.

A given design of a fixed-bearing knee prosthesis is typically made commercially available in a variety of different sizes, particularly in a variety of different widths. This is done to accommodate the many variations in patient size and anatomy across a population. However, the configuration of the fixed-knee prosthesis 10 of the present disclosure allows for a high degree of flexibility in regard to the sizing of the tibial tray 14 and the bearing 16. In particular, FIG. 5 is a diagrammatic representation of a plurality of differently-sized tibial trays 14 superimposed upon one another. As can be seen, despite each of the individual trays 14 having a size (e.g., width) that is different from the other trays 14 of the group, the basic configuration of the posterior buttress 44 and the anterior buttress 64 remains the same across the range of differently-sized trays 14. Specifically, the location of the undercuts 54, 56 defined in posterior buttress 44, respectively, remains the same across the range of differently-sized trays 14. Even though the posterior undercuts 54, 56 remain in the same location across the range of differently-sized trays 14, the width of the arms 46, 48 is varied to accommodate the overall width of a given tray 14. In a similar manner, the location of the undercuts 74, 76 defined in anterior buttress 64, respectively, remains the same across the range of differently-sized trays 14, although the width of the arms 66, 68 is varied to accommodate the overall width of a given tray 14. As shown in FIG. 5, the size and configuration of the third arms 52, 72 of the posterior buttress 44 and the anterior buttress 64, respectively, remain unchanged across the range of differently-sized trays 14.

Differently-sized bearings 16 may also be configured in such a manner. In particular, a plurality of the bearings 16 may be designed with each of such a plurality of bearings 16 having a different size, particularly a different width. However, each of such differently-sized bearings 16 may include mating features that are commonly-sized and commonly-located with the commonly-sized and commonly-located features of the tibial tray 14 described above. In particular, each of the bearings 16 across a range of differently-sized bearings 16 may include a posterior recess 78 and an anterior recess 80 that is positioned and sized to tightly fit against the edges of the posterior buttress 44 and the anterior buttress 64, respectively, of each of the tibial trays 14 across the range of differently-sized trays 14.

The posterior tabs 40 are commonly-sized and commonly-located across the range of differently-sized bearings 16 so that they are positioned in the respective posterior undercuts 54, 56 of each of the tibial trays 14 across the range of differently-sized trays 14. Likewise, the anterior tabs 42 are commonly-sized and commonly-located across the range of differently-sized bearings 16 so that they are positioned in the respective anterior undercuts 74, 76 of each of the tibial trays 14 across the range of differently-sized trays 14.

It should be appreciated from the above-discussion that the general configuration of the buttresses 44, 64 (including contiguous variations thereof) is the same across the range of differently-sized tibial trays 14. Likewise, the general configuration of the recesses 78, 80 (including contiguous variations thereof) and the general configuration of tabs 40, 42 are the same across the range of differently-sized bearings 16. As such, any size bearing 16 may be secured to any size tibial tray 14. This provides the orthopaedic surgeon with greater flexibility of matching the knee prosthesis 10 to a particular patient's anatomy.

As shown in FIGS. 6-9, other configurations of the posterior buttress 44 and the anterior buttress 64 are also contemplated. For example, in the illustrative embodiment of FIG. 6, the third arm 52 of the posterior buttress 44 and the third arm 72 of the anterior buttress 64 are configured to define a contiguous structure having a substantially constant width throughout its entire length. It should be appreciated that the recesses 78, 80 defined in the lower surface 36 of the bearing 16 are likewise reshaped in the embodiment of FIG. 6 to accommodate the different shape of the buttresses 44, 64 of the tibial tray 14. In other words, while it's contemplated that the design of the buttresses 44, 64 may be altered, it is also contemplated that the design of the recesses 78, 80 is altered accordingly to compliment the configuration of the buttresses 44, 64. It is also contemplated that the general configuration of the buttresses 44, 64 of FIG. 6, along with the corresponding configuration of the recesses 78, 80 and tabs 40, 42 of the complimentary bearing 16, may also remain the same across a range of differently-sized trays 14 and bearings 16 to accommodate the interchangeability of various sizes of trays and bearings in a similar manner to as described above in regard to FIG. 5.

Figure 7:
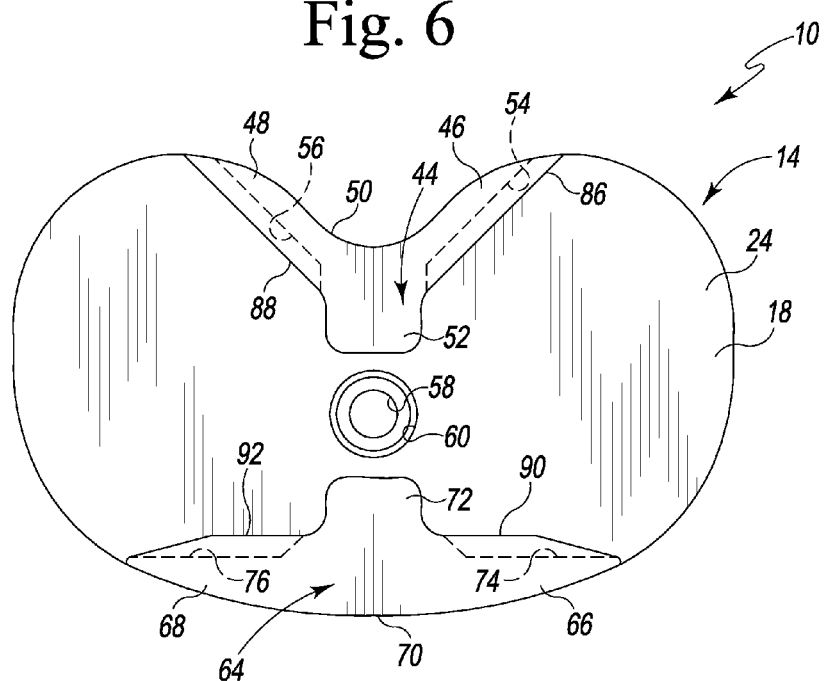

As shown in the illustrative embodiment of FIG. 7, the third arm 52 of the posterior buttress 44 is not contiguous with the third arm 72 of the anterior buttress 64. In other words, there is a gap between the arms 52, 72. It should be appreciated that the recesses 78, 80 defined in the lower surface 36 of the bearing 16 are likewise reshaped in the embodiment of FIG. 7 to accommodate the different shape of the buttresses 44, 64 of the tibial tray 14. In other words, the design of the recesses 78, 80 is altered to compliment the configuration of the separated buttresses 44, 64. It is also contemplated that the general configuration of the separated buttresses 44, 64 of FIG. 7, along with the corresponding configuration of the recesses 78, 80 and tabs 40, 42 of the complimentary bearing 16, may also remain the same across a range of differently-sized trays 14 and bearings 16 to accommodate the interchangeability of various sizes of trays and bearings in a similar manner to as described above in regard to FIG. 5.

Figure 8:
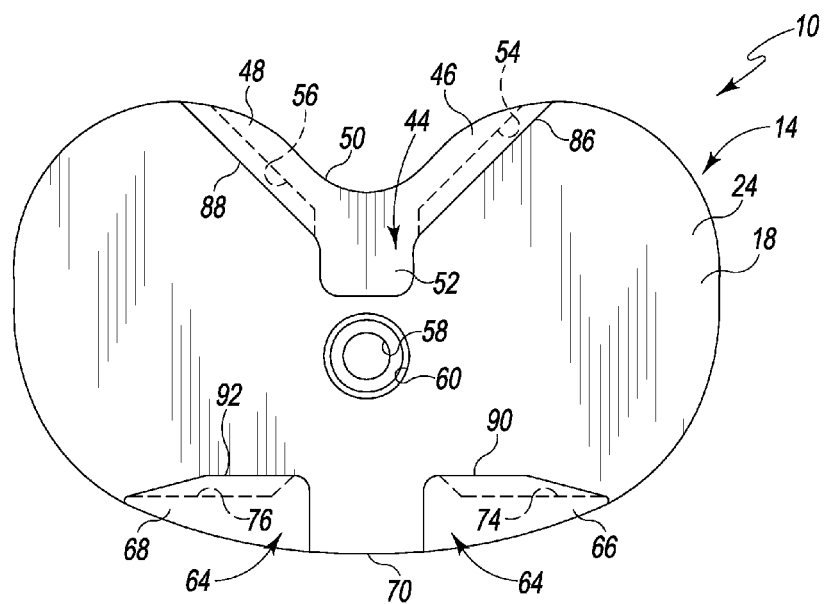

Turning to the embodiment of FIG. 8, the anterior buttress 64 is configured without the third arm 72. Moreover, the lateral arm 66 of the anterior buttress is spaced apart from the medial arm 68—i.e., there is a gap between the arms 66, 68. It should be appreciated that the recesses 78, 80 defined in the lower surface 36 of the bearing 16 are likewise reshaped in the embodiment of FIG. 8 to accommodate the different shape of the buttresses 44, 64 of the tibial tray 14. In other words, the design of the recesses 78, 80 is altered to compliment the configuration of the buttresses 44, 64. It is also contemplated that the general configuration of the buttresses 44, 64 of FIG. 8, along with the corresponding configuration of the recesses 78, 80 and tabs 40, 42 of the complimentary bearing 16, may also remain the same across a range of differently-sized trays 14 and bearings 16 to accommodate the interchangeability of various sizes of trays and bearings in a similar manner to as described above in regard to FIG. 5.

Figure 9:
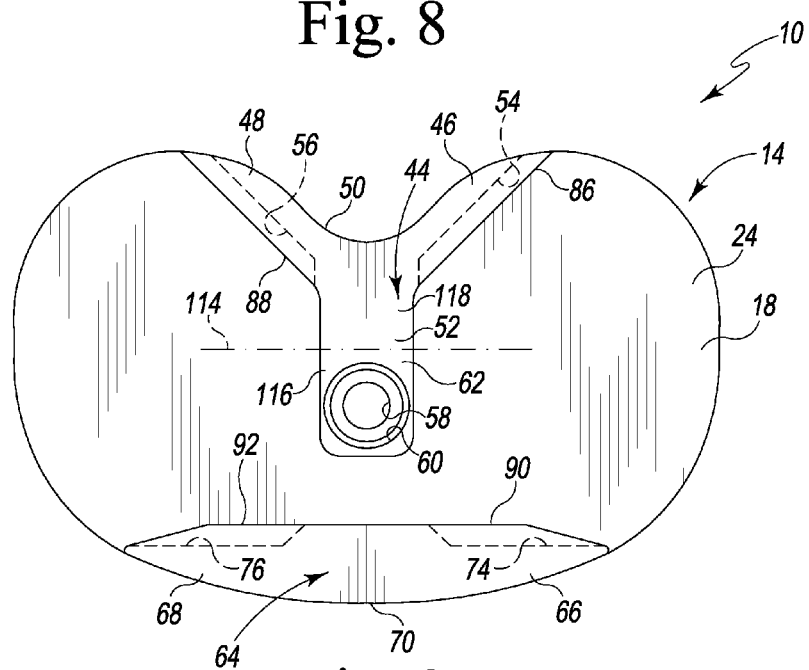
Figure 10:
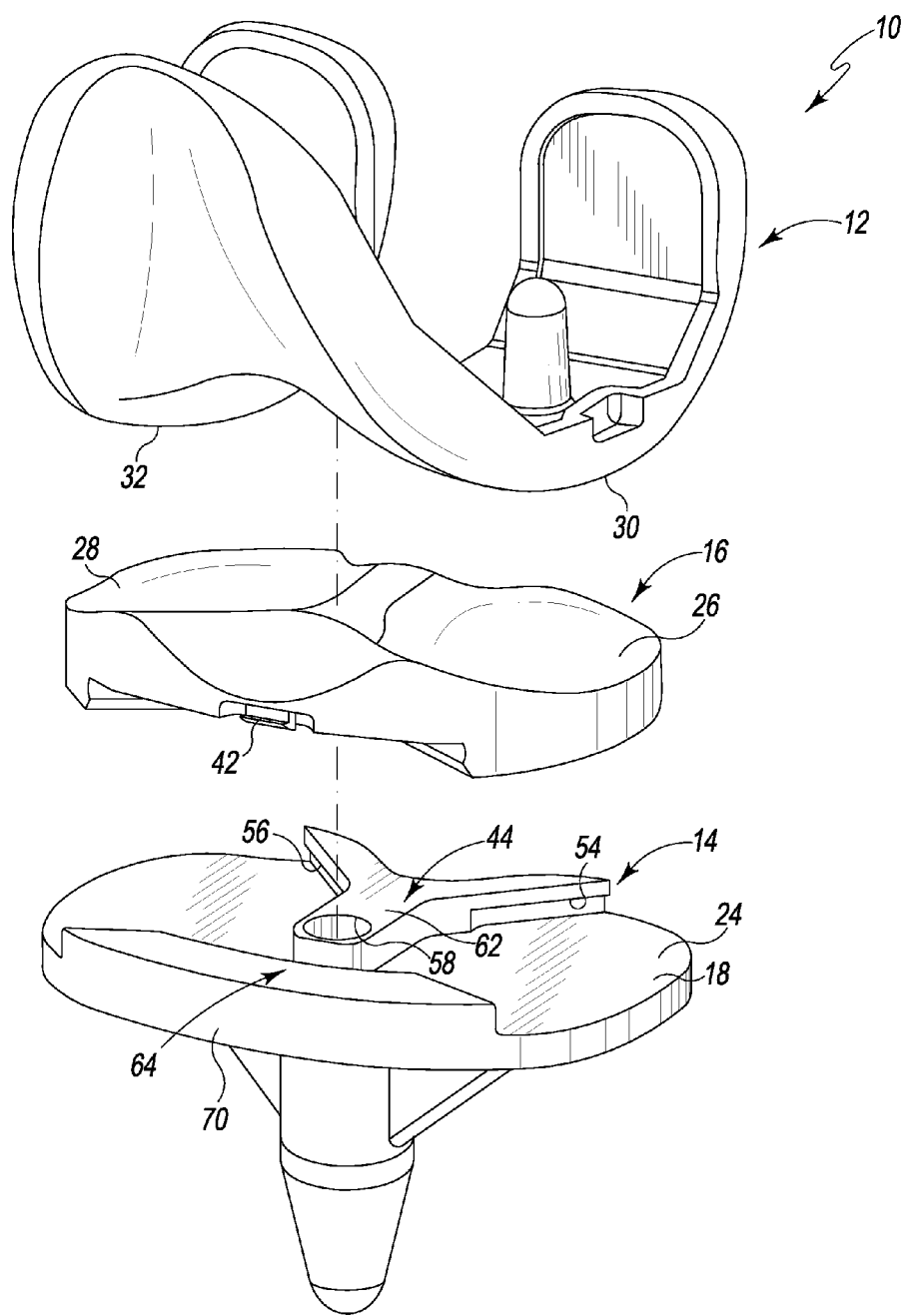
FIGS. 10-14 are similar to FIGS. 1-5, respectively, but showing another embodiment of a fixed-bearing knee prosthesis.

Yet another embodiment of the knee prosthesis 10 is shown in FIG. 9. Like the embodiment of FIG. 8, the anterior buttress 64 is configured without the third arm 72. However, unlike the design of FIG. 8, the lateral arm 66 of the anterior buttress is not spaced apart from the medial arm 68, but rather is contiguous therewith. Moreover, the third arm 52 of the posterior buttress 44 is longer than that of the embodiment shown in FIG. 8. As with the other embodiments described herein, it should be appreciated that the recesses 78, 80 defined in the lower surface 36 of the bearing 16 are likewise reshaped in the embodiment of FIG. 9 to accommodate the different shape of the buttresses 44, 64 of the tibial tray 14. In other words, the design of the recesses 78, 80 is altered to compliment the configuration of the buttresses 44, 64. It is also contemplated that the general configuration of the buttresses 44, 64 of FIG. 9, along with the corresponding configuration of the recesses 78, 80 and tabs 40, 42 of the complimentary bearing 16, may also remain the same across a range of differently-sized trays 14 and bearings 16 to accommodate the interchangeability of various sizes of trays and bearings in a similar manner to as described above in regard to FIG. 5.

Figure 13:
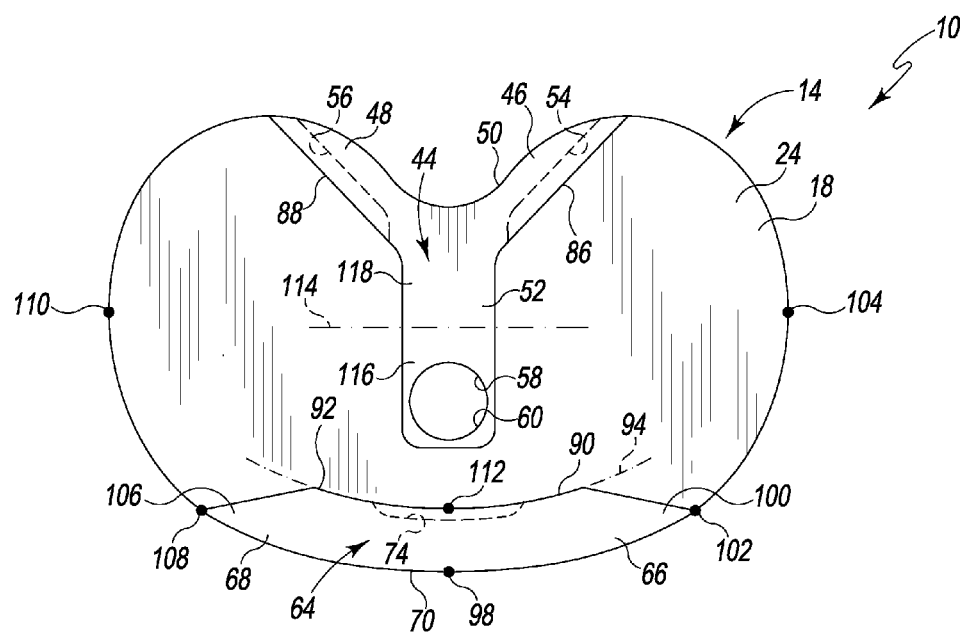

A further embodiment of the knee prosthesis 10 is shown in FIGS. 10-14. Like the embodiment of FIGS. 8 and 9, the anterior buttress 64 is configured without the third arm 72. Like the design of FIG. 9, the lateral arm 66 of the anterior buttress 64 is contiguous with the medial arm 68 of the anterior buttress 64. Specifically, as shown in FIG. 13, the anterior buttress 64 defines a continuous, monolithic structure in which proximal ends of the lateral and medial arms 66, 68 are conjoined (i.e., spatially secured to one another) at location on the anterior edge 70 at the anterior-most point 98 of the tray's platform 18. The lateral arm 66 extends laterally away from the anterior-most point 98 of the tray's platform and terminates at its lateral end 100 located at a point 102 on the anterior edge 70 of the platform 18 between the anterior-most point 98 of the tray's platform and the lateral-most point 104 of the tray's platform. The medial arm 68 extends medially away from the anterior-most point 98 of the tray's platform and terminates at its medial end 106 located at a point 108 on the anterior edge 70 of the platform 18 between the anterior-most point 98 of the tray's platform and the medial-most point 110 of the tray's platform.

Unlike the design of FIG. 9, the posterior-most edge of the anterior buttress 64 of the design of FIGS. 10-14 is curved (i.e., arcuate-shaped). In particular, as shown most clearly in FIG. 13, the imaginary line 94 extending along the posterior-most edge 90 of the lateral arm 66 and the posterior-most edge 92 of the medial arm 68 is curved along a constant radius. It should be appreciated that since the arms 66, 68 of the anterior buttress 64 are contiguous, the posterior-most edge 90 of the lateral arm 66 and the posterior-most edge 92 of the medial arm 68 define a single, continuous, uninterrupted edge.

Moreover, the anterior buttress 64 of the design of the knee prosthesis 10 shown in FIGS. 10-14 includes a single anterior undercut 74 (i.e., the second undercut 76 has been omitted). The anterior undercut 74 is centered on the intersection of the two arms 66, 68 defining the anterior buttress 64. In other words, the imaginary line 94 extending along the posterior-most edge 90 of the lateral arm 66 and the posterior-most edge 92 of the medial arm 68 has a midpoint 112. The anterior undercut 74 is centered on the midpoint 112. It should be appreciated that the lower surface 36 of the bearing 16 includes a single anterior tab 42 sized and positioned to be received into the single anterior undercut 74 (see FIG. 11).

Figure 11:
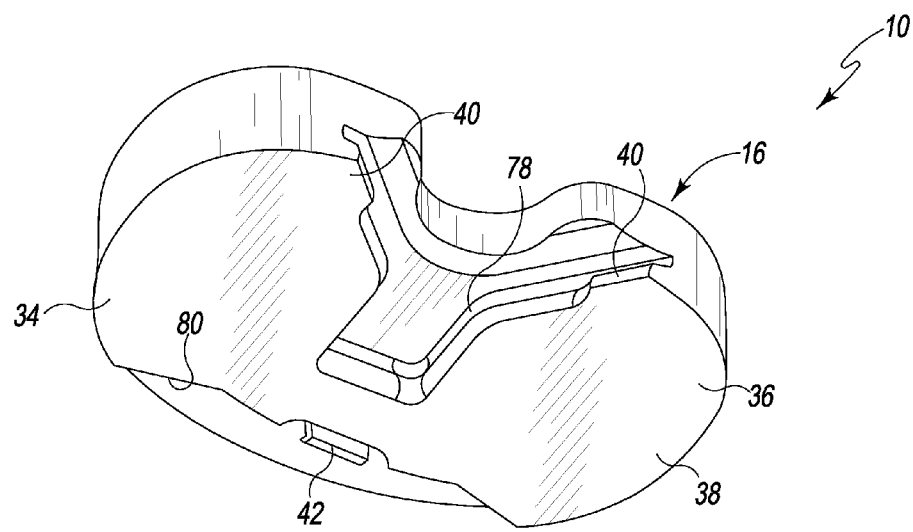

Like the designs of FIGS. 7-9, the anterior buttress 64 of the knee prosthesis 10 shown in FIGS. 10-14 is discontiguous with the posterior buttress 44. In other words, the buttresses 44, 64 are spaced apart from one another such that there is a gap therebetween. As with the other embodiments described herein, it should be appreciated that the recesses 78, 80 defined in the lower surface 36 of the bearing 16 are likewise reshaped in the embodiment of FIGS. 10-14 (relative to the embodiments of FIGS. 1-9) to accommodate the different shape of the buttresses 44, 64 of the tibial tray 14. In other words, as shown in FIG. 11, the design of the recesses 78, 80 is altered to compliment the configuration of the buttresses 44, 64.

Figure 14:
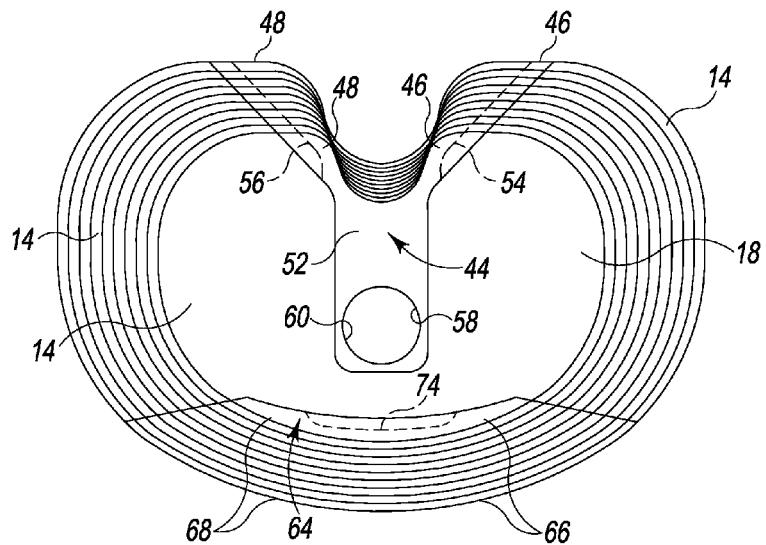

Moreover, as shown in FIG. 14, the general configuration of the buttresses 44, 64 of FIGS. 10-13, along with the corresponding configuration of the recesses 78, 80 and tabs 40, 42 of the complimentary bearing 16, remain the same across a range of differently-sized trays 14 and bearings 16 to accommodate the interchangeability of various sizes of trays and bearings in a similar manner to as described above in regard to FIG. 5.

As described herein, the various designs of the knee prosthesis 10 allow for the enhanced interchangeability of differently-sized components. In particular, any one of a plurality of differently-sized bearings may be secured to any one of a plurality of differently-sized tibial trays. As a result, articulation surface geometries and other features of the bearing may be enhanced for each size of femoral component. Such interchangeability also allows for smaller size increments in the design of a range of femoral components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. A fixed-bearing knee prosthesis, comprising:
a femoral component having a medial condyle surface and a lateral condyle surface,
a bearing having (i) a medial bearing surface configured to articulate with the medial condyle surface of the femoral component, and (ii) a lateral bearing surface configured to articulate with the lateral condyle surface of the femoral component, and
a tibial tray secured to the bearing, the tibial tray having a platform with a fixation member extending downwardly from a lower surface thereof, the platform having (i) a posterior buttress extending along a posterior section of a perimeter of the platform and extending upwardly from an upper surface of the platform, (ii) an anterior buttress extending along an anterior section of the perimeter of the platform and extending upwardly from the upper surface of the platform, and (iii) an elongated bore having a superior end that opens into an upper surface of the posterior buttress,
wherein the anterior buttress has (i) a first arm extending along an anterior edge of the platform, (ii) a second arm extending along the anterior edge of the platform in a direction away from the first arm of the anterior buttress, the second arm being contiguous with the first arm, and (iii) an undercut defined therein,
wherein the posterior buttress is generally Y-shaped and has (i) a first arm extending along a posterior edge of the platform and having a first undercut defined therein, (ii) a second arm extending along the posterior edge of the platform in a direction away from the first arm and having a second undercut defined therein, and (iii) a third arm extending anteriorly away from the first arm and the second arm, and
wherein (i) a first imaginary line extends along a lateral-most edge of the first arm of the posterior buttress, (ii) a second imaginary line extends along a medial-most edge of the second arm of the posterior buttress and intersects the first imaginary line to define an angle of intersection therebetween, and (iii) the angle of intersection is between 45-145°.

2. The knee prosthesis of claim 1, wherein the angle of intersection is approximately 60-120°.

3. The knee prosthesis of claim 1, wherein the angle of intersection is approximately 90°.

4. The knee prosthesis of claim 1, wherein the superior end of the elongated bore opens into the third arm of the posterior buttress.

5. The knee prosthesis of claim 1, wherein:
the fixation member of the tibial tray comprises an elongated stem extending downwardly from the lower surface of the platform, and
the elongated bore extends away from the upper surface of the posterior buttress in the direction toward a distal end of the stem.

6. The knee prosthesis of claim 1, wherein the elongated bore of the tibial tray extends in the superior/inferior direction.

7. The knee prosthesis of claim 1, wherein:
a third imaginary line extends in a medial/lateral direction and bisects the third arm of the posterior buttress so as to divide the third arm of the posterior buttress into an anterior half and a posterior half, and
the superior end of the elongated bore of the tibial tray opens into the upper surface of the posterior buttress at a location in the anterior half of the third arm of the posterior buttress.

8. The knee prosthesis of claim 1, wherein:
the bearing has an upper surface and a lower surface,
both the medial bearing surface and the lateral bearing surface are defined in the upper surface of the bearing,
the lower surface of the bearing contacts the upper surface of the platform,
the lower surface of the platform has a posterior recess and an anterior recess formed therein, and
the posterior buttress is positioned in the posterior recess and the anterior buttress is positioned in the anterior recess.

9. The knee prosthesis of claim 8, wherein the posterior buttress is discontiguous with the anterior buttress.

10. A fixed-bearing knee prosthesis, comprising:
a femoral component having a medial condyle surface and a lateral condyle surface,
a bearing having (i) a medial bearing surface configured to articulate with the medial condyle surface of the femoral component, and (ii) a lateral bearing surface configured to articulate with the lateral condyle surface of the femoral component, and
a tibial tray secured to the bearing, the tibial tray having a platform with a fixation member extending downwardly from a lower surface thereof, the platform having (i) a posterior buttress extending along a posterior section of a perimeter of the platform and extending upwardly from an upper surface of the platform, (ii) an anterior buttress extending along an anterior section of the perimeter of the platform and extending upwardly from the upper surface of the platform, and (iii) an elongated bore having a superior end that opens into an upper surface of the posterior buttress,
wherein the posterior buttress is generally Y-shaped and has (i) a first arm extending along a posterior edge of the platform and having a first undercut defined therein, (ii) a second arm extending along the posterior edge of the platform in a direction away from the first arm and having a second undercut defined therein, and (iii) a third arm extending anteriorly away from the first arm and the second arm, wherein the anterior buttress has (i) a first arm extending along an anterior edge of the platform, (ii) a second arm extending along the anterior edge of the platform in a direction away from the first arm of the anterior buttress, and (iii) an undercut defined therein, and wherein (i) an imaginary line extends along a posterior-most edge of the first arm of the anterior buttress and a posterior-most edge of the second arm of the anterior buttress, and (ii) the imaginary line defines a curve having a constant radius.

11. The knee prosthesis of claim 10, wherein the superior end of the elongated bore opens into the third arm of the posterior buttress.

12. The knee prosthesis of claim 10, wherein:
the fixation member of the tibial tray comprises an elongated stem extending downwardly from the lower surface of the platform, and
the elongated bore extends away from the upper surface of the posterior buttress in the direction toward a distal end of the stem.

13. The knee prosthesis of claim 10, wherein the elongated bore of the tibial tray extends in the superior/inferior direction.

14. The knee prosthesis of claim 10, wherein:
a third imaginary line extends in a medial/lateral direction and bisects the third arm of the posterior buttress so as to divide the third arm of the posterior buttress into an anterior half and a posterior half, and
the superior end of the elongated bore of the tibial tray opens into the upper surface of the posterior buttress at a location in the anterior half of the third arm of the posterior buttress.

15. The knee prosthesis of claim 10, wherein:
the bearing has an upper surface and a lower surface,
both the medial bearing surface and the lateral bearing surface are defined in the upper surface of the bearing,
the lower surface of the bearing contacts the upper surface of the platform,
the lower surface of the platform has a posterior recess and an anterior recess formed therein, and
the posterior buttress is positioned in the posterior recess and the anterior buttress is positioned in the anterior recess.

16. The knee prosthesis of claim 10, wherein the posterior buttress is discontiguous with the anterior buttress.

17. A fixed-bearing knee prosthesis, comprising:
a femoral component having a medial condyle surface and a lateral condyle surface,
a tibial tray having a platform with a fixation member extending downwardly from a lower surface thereof, the platform having (i) a generally Y-shaped posterior buttress extending upwardly from an upper surface of the platform and having a pair of arms extending along a posterior section of a perimeter of the platform, each of the pair of arms having an undercut defined therein, and (ii) an anterior buttress extending along an anterior section of the perimeter of the platform and extending upwardly from the upper surface of the platform, the anterior buttress being discontiguous with the posterior buttress and having an undercut defined therein, and (iii) an elongated bore having a superior end that opens into an upper surface of the posterior buttress, and
a plurality of bearings configured to be separately secured to the tibial tray, wherein each of the plurality of bearings has (i) a width that is different from at least some of the other of the plurality of bearings, (ii) an upper surface having a medial bearing surface configured to articulate with the medial condyle surface of the femoral component and a lateral bearing surface configured to articulate with the lateral condyle surface of the femoral component, (iii) a lower surface having a posterior recess defined therein to receive the posterior buttress and an anterior recess defined therein to receive the anterior buttress, (iv) a pair of posterior locking tabs arranged to be respectively received in the undercuts defined in each of the pair of arms of the posterior buttress, and (v) an anterior locking tab arranged to be received in the undercut defined in the anterior buttress.

18. The knee prosthesis of claim 17, wherein:
the fixation member of the tibial tray comprises an elongated stem extending downwardly from the lower surface of the platform, and
the elongated bore extends away from the upper surface of the posterior buttress in the direction toward a distal end of the stem.

19. The knee prosthesis of claim 17, wherein the elongated bore of the tibial tray extends in the superior/inferior direction.

* * * * *